(12) United States Patent
Fuchigami et al.

(10) Patent No.: US 11,866,590 B2
(45) Date of Patent: Jan. 9, 2024

(54) DIISOCYANATE-BASED RADICAL POLYMERIZABLE SILANE COUPLING COMPOUND HAVING AN URETHANE BOND

(71) Applicant: KABUSHIKI KAISHA SHOFU, Kyoto (JP)

(72) Inventors: Kiyomi Fuchigami, Kyoto (JP); Kenzo Yamamoto, Kyoto (JP); Naoya Kitada, Kyoto (JP); Kazuya Shinno, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 524 days.

(21) Appl. No.: 17/279,337

(22) PCT Filed: Sep. 25, 2019

(86) PCT No.: PCT/JP2019/037571
§ 371 (c)(1),
(2) Date: Mar. 24, 2021

(87) PCT Pub. No.: WO2020/067146
PCT Pub. Date: Apr. 2, 2020

(65) Prior Publication Data
US 2021/0395532 A1 Dec. 23, 2021

(30) Foreign Application Priority Data

Sep. 28, 2018 (JP) .................................. 2018-183399
Sep. 28, 2018 (JP) .................................. 2018-183400

(51) Int. Cl.
*C09C 3/12* (2006.01)
*A61K 6/60* (2020.01)
*C07F 7/18* (2006.01)
*C08F 292/00* (2006.01)

(52) U.S. Cl.
CPC .................. *C09C 3/12* (2013.01); *A61K 6/60* (2020.01); *C07F 7/1804* (2013.01); *C08F 292/00* (2013.01)

(58) Field of Classification Search
None
See application file for complete search history.

(56) References Cited

U.S. PATENT DOCUMENTS

| 5,192,815 A * | 3/1993 | Okada | A61K 6/887 |
| | | | 523/213 |
| 2015/0344504 A1* | 12/2015 | Klun | C09J 133/14 |
| | | | 428/1.51 |

FOREIGN PATENT DOCUMENTS

| CN | 104768956 | 7/2015 |
| JP | 2-134307 | 5/1990 |
| JP | 3-70778 | 3/1991 |
| JP | 2007-238567 | 9/2007 |
| JP | 2010-229054 | 10/2010 |
| JP | 2015-196682 | 11/2015 |
| JP | 2015-196684 | 11/2015 |
| JP | 2015-196685 | 11/2015 |
| JP | 2016-194027 | 11/2016 |
| KR | 10-2017-0128955 | 11/2017 |

OTHER PUBLICATIONS

International Search Report (ISR) dated Nov. 26, 2019 in International (PCT) Application No. PCT/JP2019/037571.
International Preliminary Report on Patentability dated Mar. 23, 2021 in International (PCT) Patent Application No. PCT/JP2019/037571.

* cited by examiner

Primary Examiner — Peter A Salamon
(74) Attorney, Agent, or Firm — Wenderoth, Lind & Ponack, L.L.P.

(57) ABSTRACT

The present invention relates to a novel diisocyanate-based radical polymerizable silane coupling compound having an urethane bond and a medical and/or dental curable composition comprising the same. The present invention provides a novel silane coupling agent that imparts high affinity to a radical polymerizable monomer, thereby imparting high mechanical strength and durability when used for a medical and/or dental curable composition, and an inorganic filler surface-treated with the novel silane coupling agent and a novel medical and/or dental curable composition.

4 Claims, No Drawings

DIISOCYANATE-BASED RADICAL POLYMERIZABLE SILANE COUPLING COMPOUND HAVING AN URETHANE BOND

TECHNICAL FIELD

The present invention relates to a novel diisocyanate-based radical polymerizable silane coupling compound having an urethane bond and a medical and/or dental curable composition comprising the same.

BACKGROUND ART

In the medical and/or dental field, metal prosthetic appliances and synthetic resin molded articles and the like have been used for repair of defects in bones and teeth. For adhesion thereof to living hard tissues, an adhesive containing an adhesive polymerizable monomer has been frequently used. In the medical and/or dental field, a medical and/or dental curable composition, so-called composite resin, has been used in clinical settings on a daily basis. An uncured body (before radical polymerization) paste is filled in a defect part such as teeth, and then external energy such as photoirradiation is imparted, thus obtaining a radical polymerization cured body.

Generally, in these adhesives and composite resins, (meth)acrylic acid derivative monomers such as methyl methacrylate, triethylene glycol dimethacrylate and urethan-based dimethacrylate have been used. In free radical polymerization (hereinafter referred to as radical polymerization) of vinyl monomers such as these (meth)acrylic acid derivative monomers, a carbon-carbon double bond is cleaved to become a single bond, thus forming a polymer and leading to cure. To this composite resin, not only vinyl monomers but also inorganic fillers are added for the purpose of improving the mechanical strength. Generally, these inorganic fillers are surface-treated with a silane coupling agent having a polymerizable group to attempt to improve the wettability and to improve the mechanical strength. In the medical and/or dental field, conventionally γ-methacryloxy-propyltrimethoxysilane (hereinafter referred to as KBM-503) as the silane coupling agent has been widely used. When a particle that is surface-treated with the compound is used, there were problems that hydrolysis tends to progress due to low hydrophobicity and that the durability of the material is low. Also, since the filling ratio of inorganic fillers was low due to its low hydrophobicity, there was a drawback that sufficient mechanical strength cannot be obtained.

When the basic framework of the (meth)acrylic acid derivative monomer used in the composite resin is an ethylene glycol chain or an alkylene chain, a silane coupling agent such as KBM-503 may be used to improve wettability and mechanical strength to some extent.

Therefore, in order to improve the durability and filling rate of the material, a method for using a silane coupling agent having a long alkyl chain (Patent literatures 1 to 3), a method for using a silane coupling agent using a fluoroalkylene group (Patent literature 4) and a method for using a silane coupling agent having many polymerizable groups (Patent literature 5) have been proposed.

PRIOR LITERATURE

Patent Literature

Patent literature 1: JP 2-134307 A
Patent literature 2: JP 3-70778 A
Patent literature 3: JP 2015-196682 A
Patent literature 4: JP 2007-238567 A
Patent literature 5: JP 2010-229054 A

SUMMARY OF INVENTION

Technical Problem

When the method mentioned in Patent literatures 1 to 3 was applied to a medical and/or dental composite resin, which is one of medical and/or dental curable compositions, there was a room for improvement in the mechanical strength. In addition, when the method mentioned in Patent literature 4 was applied to a medical and/or dental material, the water resistance was low and the durability of the material was insufficient. Thus, it is insufficient to achieve both the durability and the mechanical strength of a material that used a silane coupling agent of the prior art was insufficient, and there was a room for further improvement.

The conventional method using hydrosilylation reaction in the synthesis of silane coupling agents requires expensive precious metal catalysts such as platinum and palladium, and it might cause yellowing of the cured material due to residual precious metal catalysts. One synthetic method not using the hydrosilylation reaction is to introduce radical polymerizable groups and alkoxysilane groups within a single molecule by reacting isocyanate groups with compounds having hydroxy groups on both ends. For example, it is possible to synthesize the silane coupling agent by reacting decane-1,10-diol, 2-isocyanate ethyl methacrylate and (3-isocyanate-propyl)trimethoxysilane in tetrahydrofuran solvent. However, the good solvents for compounds such as alkyl diols and polyethylene glycols are only hydrophilic low-boiling compounds such as acetone and tetrahydrofuran, and hydrophobic high-boiling solvents such as toluene cannot solve them. Therefore, it is necessary to remove the water dissolved in such an acetone and tetrahydrofuran before use. In addition, the low boiling point required a long time for the urethane reaction between the isocyanate group and the hydroxy group. In addition, as the molecular weight of diols etc. increases, their melting points became higher than room temperature and make it difficult to perform the reaction in neat (solvent-free) conditions.

It is an object of the present invention to provide a novel silane coupling agent that imparts high affinity to a radical polymerizable monomer having an urethane group, thereby imparting high mechanical strength, and durability when used for a medical and/or dental curable composition, and an inorganic filler surface-treated with the novel silane coupling agent and a novel medical and/or dental curable composition. Furthermore, as no hydrosilylation reaction is used in the synthesis of the silane coupling agent and no yellowing of the cured material occurs due to the residual precious metal catalyst, it is also an object to provide excellent color stability of the cured material.

Means to Solve the Problem

The inventors of the present application have intensively studied and found that high affinity to a radical polymerizable monomer is imparted by surface-treating an inorganic filler with a silane coupling agent represented by a following chemical structure. This enabled to imparting high mechanical strength when the silane coupling agent is used for a medical and/or dental curable composition.

[Chemical Formula 1]

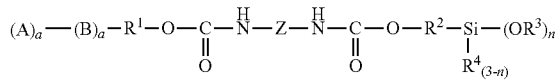

In the above chemical formula,
A represents a $H_2C=CH-$, $H_2C=C(CH_3)-$, or $H_2C=CH-C_6H_4-$ group where $C_6H_4$ represents a phenylene group,
B represents a $-C(O)-O-$, $-C(O)-S-$, $-C(O)-NH-$, $-NH-C(O)-NH-$, $-NH-C(O)-S-$, or $-NH-C(O)-O-$ group,
$R^1$ represents a C2 to C100 linear or branched alkylene group and may comprise one or more of a $-O-CH_2-CH_2-$, $-O-CH(CH_3)-CH_2-$ and/or $-CH(CH_3)-CH_2-O-$ groups,
Z comprises at least one or more of a benzene ring or a cyclohexane ring and/or a C2 to C100 linear or branched alkylene group,
$R^2$ represents a C2 to C100 linear or branched alkylene group,
$R^3$ represents a C1 to C6 linear or branched alkyl group,
$R^4$ represents a C1 to C16 linear or branched alkyl group, a phenyl group, or a halogen atom, and when n is 0, at least one or more halogen atoms are bonded to Si,
a is 1 to 6 and
n is 0 to 3.

Effect of the Invention

By surface-treating an inorganic filler with the silane coupling agent of the present invention, high affinity to a radical polymerizable monomer is expressed, thus imparting high mechanical strength, flexibility and pressure-sensitive adhesion/adhesion to a medical and/or dental curable composition. In addition, since no hydrosilylation reaction is used in the synthesis of the silane coupling agent and no yellowing of the cured material occurs due to the residual precious metal catalyst, excellent color stability of the cured material is provided.

This high affinity effect remarkably appears when a radical polymerizable monomer has an urethane group. This is considered to be due to the fact that there are two urethane bonds in formula [Chemical Formula 1]. In other words, an inorganic filler surface-treated with the silane coupling agent of the present invention has a surface on which an urethane group is introduced, which is considered to express remarkable high affinity to a radical polymerizable monomer having an urethane group.

In addition, since the silane coupling compounds in the present invention use an aliphatic diisocyanate and/or a cyclic compound backbone diisocyanate as the reaction substrate, for which toluene or the like is a good solvent, the number of organic selectable solvents increases in comparison with organic-solvent-poor-solubility compounds such as 1-10-decanediol. As a result, a higher temperature can be selected for the urethane reaction.

DETAILED DESCRIPTION OF THE INVENTION

The molecular structure of the silane coupling agent having a radical polymerizable group in the present invention is the structure shown in [Chemical Formula 2], and may be used in alone or combinations of two or more.

The structure shown in [Chemical Formula 2] is described in more detail.
A represents a $H_2C=CH-$, $H_2C=C(CH_3)-$, or $H_2C=CH-C_6H_4-$ group where $C_6H_4$ represents a phenylene group,
B represents a $-C(O)-O-$, $-C(O)-S-$, $-C(O)-NH-$, $-NH-C(O)-NH-$, $-NH-C(O)-S-$, or $-NH-C(O)-O-$ group,
$R^1$ represents a C2 to C100 (preferably C2 to C40, more preferably C2 to C25, even more preferably C2 to C12) linear or branched alkylene group and can comprise one or more of a $-O-CH_2-CH_2-$, $-O-CH(CH_3)-CH_2-$, and $-CH(CH_3)-CH_2-O-$ groups,
Z comprises or consists of at least one or more of a benzene ring or a cyclohexane ring and/or a C2 to C100 linear or branched alkylene group,
$R^2$ represents a C2 to C100 (preferably C2 to C40, more preferably C2 to C25, even more preferably C2 to C12) linear or branched alkylene group,
$R^3$ represents a C1 to C6 linear or branched alkyl group,
$R^4$ represents a C1 to C16 linear or branched alkyl group, a phenyl group, or a halogen atom, and when n is 0, at least one or more halogen atoms are bonded to Si,
a is 1 to 6 and
n is 0 to 3.

[Chemical Formula 2]

$(A)_a-(B)_a-R^1-O-\underset{\underset{O}{\|}}{C}-\underset{H}{N}-Z-\underset{H}{N}-\underset{\underset{O}{\|}}{C}-O-R^2-\underset{\underset{R^4_{(3-n)}}{|}}{Si}-(OR^3)_n$ When an inorganic filler is surface-treated using the silane coupling agent of the embodiments of the present invention, the treatment concentration is generally preferably 0.05 mass time to 10 mass times the concentration of the inorganic filler although it depends on the density (mol/g) of the silanol group of the mother particle. Treatment with a concentration lower than 0.05 mass time is not preferable since the silane coupling agent cannot be sufficiently introduced, and a treatment with a concentration exceeding 10 mass times is not preferable since a condensate of only the silane coupling agent is produced, affecting the mechanical strength.

The chemical structures of representative silane coupling compounds in the present invention are described below.

[Chemical Formula 3]

-continued

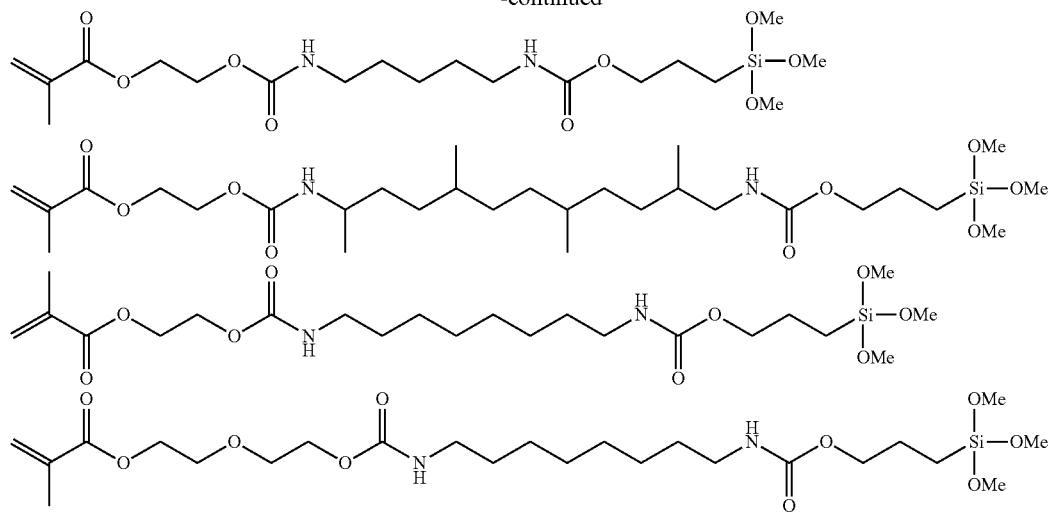

[Chemical Formula 4]

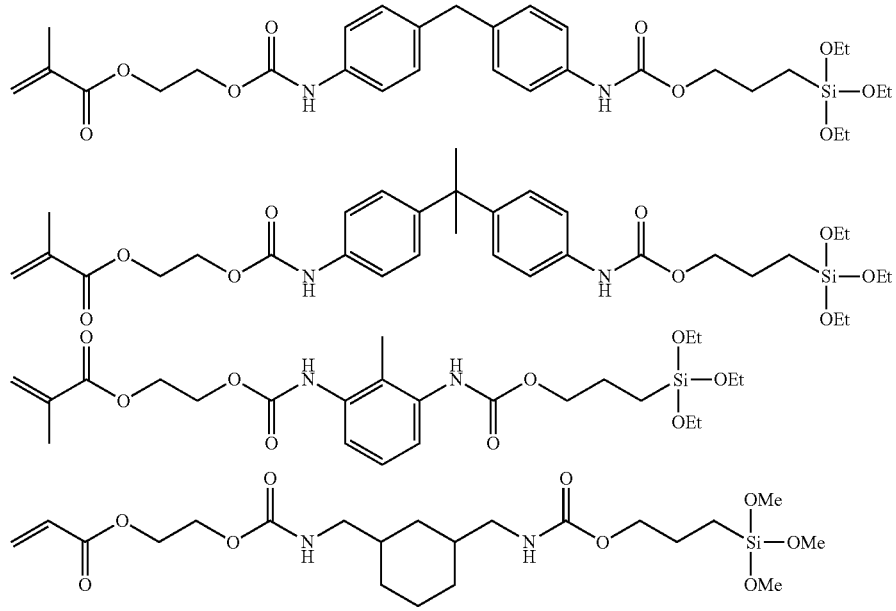

[Chemical Formula 5]

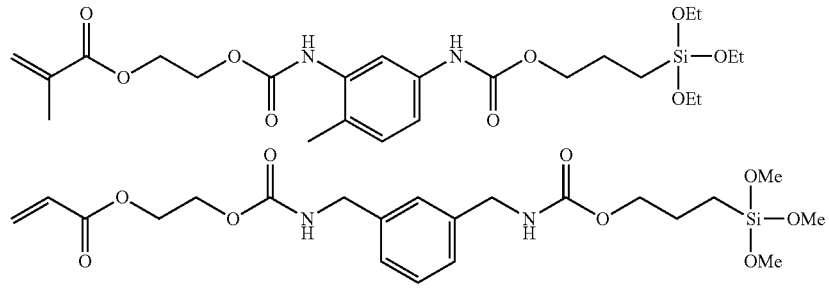

Although their chemical compositions are not particularly limited, examples of the inorganic filler treated with the silane coupling agent of the embodiments of the present invention include silicon dioxide, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass and the like. Particularly, barium fluoroaluminosilicate glass, strontium fluoroaluminosilicate glass, fluoroaluminosilicate glass and the like, which are used in dental glass ionomer cement, resin modified glass ionomer cement and resin cement and the like, can also be suitably used. The fluoroaluminosilicate glass as used herein has a basic structure of silicon oxide and aluminum oxide and contains an alkali metal for introducing non-crosslinked oxygen. The fluoroaluminosilicate glass further has an alkaline earth metal including strontium and fluorine as modified/coordinated ions. The fluoroaluminosilicate glass is also a composition in which a lanthanoid series element is incorporated into the skeleton in order to impart further radiopacity. This lanthanoid series element also participates in the composition as a modified/coordinated ion according to the composition range. These inorganic fillers may be used alone or as a mixture of two or more. The composition ratio of the inorganic filler treated with the silane coupling agent of the embodiments of the present invention in the medical and/or dental curable composition in the present invention is not particularly limited, and is preferably in the range of 25 to 90% by weight. It is not preferable that the composition ratio is 25% by weight or less since the mechanical (physical) strength of the cured product is low. It is not preferable that the composition ratio is 90% by weight or more since clinical operability is poor due to too high viscosity of the prepared paste. Furthermore, the average particle size of the inorganic filler is preferably 0.001 to 100 μm, and more preferably 0.001 to 10 μm. Furthermore, the shape of the inorganic filler may be either spherical or indefinite shape. "Average particle size" as used herein means a particle size at an integrated value of 50% in the particle size distribution determined by a laser diffraction/scattering method.

When the silane coupling agent of the embodiments of the present invention is applied to the medical and/or dental curable composition, the radical polymerizable monomer to be included is included in the medical and/or dental curable composition in the amount of preferably 10 to 60% by weight, and more preferably 15 to 30% by weight. When the amount is 10% by weight or less, the viscosity of the medical and/or dental curable composition is too high, which may cause defects, and when the ratio is 60% by weight or more, the strength of the medical and/or dental curable composition may decrease.

As the radical polymerizable monomer used in the medical and/or dental curable composition of the embodiments of the present invention, a radical polymerizable monomer that has been used in the medical and/or dental field can be used without limitation, and it is preferable that the molecular skeleton thereof has an urethan bond. The molecular skeleton thereof may have an benzene ring and/or cyclohexane ring. The urethan bond (—NH—C(O)—O—) is for effectively forming a hydrogen bond with the silane coupling agent of the embodiments of the present invention. Examples of the radical polymerizable monomer as used herein include 7,7,9-trimethyl-4,13-dioxo-3,14-dioxa-5,12-diazahexadecane-1,16-diyl dimethacrylate (UDMA) synthesized by an urethan reaction of 2,2,4-trimethylhexamethylene diisocyanate with 2-hydroxyethyl methacrylate (HEMA), radical polymerizable monomers synthesized by an urethan reaction of HEMA or hydroxyethyl acrylate (HEA) with each of 2,4-toluylenediisocyanate, hydrogenated diphenylmethane diisocyanate, naphthalene diisocyanate or hexamethylene diisocyanate, urethan diacrylates obtained by reaction with aliphatic and/or aromatic diisocyanate glycerol (meth)acrylate or 3-methacrylol-2-hydroxypropyl ester, an urethan reactant of 1,3-bis(2-isocyanate,2-propyl)benzene with a compound having a hydroxy group and the like. More specific examples thereof include 2,7,7,9,15-pentamethyl-4,13-dioxo-3,14-dioxa-5,12-diazahexadecane-1,16-diyl diacrylate, 2,7,7,9,15-pentamethyl-4,13-18-trioxo-3,14,17-trioxa-5,12-diazaicos-19-enyl methacrylate, 2,8,10,10,15-pentamethyl-4,13,18-trioxo-3,14,17-trioxa-5,12-diazaicos-19-enyl methacrylate, 2,7,7,9,15-pentamethyl-4,13-dioxo-3,14-dioxa-5,12-diazahexadecane-1,16-diylbis(2-methylacrylate), 2,2'-(cyclohexane-1,2-diylbis(methylene))bis(azanediyl)bis(oxomethylene)bis(oxy)bis(propane-2,1-diyl)diacrylate, 2-((2-(((1-(acryloyloxy)propan-2-yloxy)carbonylamino)methyl)cyclohexyl)methylcarbamoyloxy)propyl methacrylate, 2,2'-(cyclohexane-1,2-diylbis(methylene))bis(azanediyl)bis(oxomethylene)bis(oxy)bis(propane-2,1-diyl)bis(2-methylacrylate), 2,2'-(bicyclo[4.1.0]heptane-3,4-diylbis(methylene))bis(azanediyl)bis(oxomethylene)bis(oxy)bis(propane-2,1-diyl)diacrylate, 2-((4-(((1-(acryloyloxy)propan-2-yloxy)carbonylamino)methyl)bicyclo[4.1.0]heptan-3-yl)methylcarbamoyloxy)propyl methacrylate, 2,2'-(bicyclo[4.1.0]heptane-3,4-diylbis(methylene))bis(azanediyl)bis(oxomethylene)bis(oxy)bis(propane-2,1-diyl)bis(2-methylacrylate), 7,7,9-trimethyl-4,13-dioxo-3,14-dioxa-5,12-diazahexadecane-1,16-diyl diacrylate, 7,7,9-trimethyl-4,13,18-trioxo-3,14,17-trioxa-5,12-diazaicos-19-enyl methacrylate, 8,10,10-trimethyl-4,13,18-trioxo-3,14,17-trioxa-5,12-diazaicos-19-enyl methacrylate, 7,7,9-trimethyl-4,13-dioxo-3,14-dioxa-5,12-diazahexadecane-1,16-diylbis(2-methylacrylate), 4,13-dioxo-3,14-dioxa-5,12-diazahexadecane-1,16-diyl diacrylate, 4,13,18-trioxo-3,14,17-trioxa-5,12-diazaicos-19-enyl methacrylate, 4,13-dioxo-3,14-dioxa-5,12-diazahexadecane-1,16-diylbis(2-methylacrylate), 2-(1-(2-((2-(acryloyloxy)ethoxy)carbonylamino)-4,4-dimethylcyclohexyl)ethylcarbamoyloxy)ethyl methacrylate, 2-(1-(2-((2-(acryloyloxy) ethoxy) carbonylamino)ethyl)-5,5-dimethylcyclohexylcarbamoyloxy)ethyl methacrylate, 2-(2-(((1-(methacryloyloxy)propan-2-yloxy)carbonylamino)methyl)-2,5,5-trimethylcyclohexylcarbamoyloxy)propane-1,3-diylbis(2-methylacrylate), 2-(2-(((1-(methacryloyloxy)propan-2-yloxy)carbonylamino)methyl)-2,5,5-trimethylcyclohexylcarbamoyloxy)propane-1,3-diyl diacrylate, 2-(2-(((1-(acryloyloxy)propan-2-yloxy)carbonylamino)methyl)-2,5,5-trimethylcyclohexylcarbamoyloxy)propane-1,3-diylbis(2-methylacrylate), 3-(15-(2-(acryloyloxy)ethyl)-3,12,19-trioxo-2,13,18-trioxa-4,11-diazahenicos-20-enyl)pentane-1,5-diyl diacrylate, 3-(15-(2-(acryloyloxy)ethyl)-3,12,19-trioxo-2,13,18-trioxa-4,11-diazahenicos-20-enyl)pentane-1,5-diylbis(2-methylacrylate), 2,2'-(cyclihexane-1,2-diylbis(methylene))bis(azanediyl)bis(oxomethylene)bis(oxy)bis(ethane-2,1-diyl)diacrylate, 2-((2-(((2-(acryloyloxy)ethoxy)carbonylamino)methyl)cyclohexyl)methylcarbamoyloxy)ethyl methacrylate, 2,2'-(cyclihexane-1,2-diylbis(methylene))bis(azanediyl)bis(oxomethylene)bis(oxy)bis(ethane-2,1-diyl)bis(2-methylacrylate), 2,15-bis(cyclohexyloxymethyl)-4,13-dioxo-3,14-dioxa-5,12-diazahexadecane-1,16-diyl diacrylate, 2,15-bis(cyclohexyloxymethyl)-4,13-dioxo-3,14-dioxa-5,12-diazahexadecane-1,16-diylbis(2-methylacrylate), 2,15-bis(cyclohexyloxymethyl)-4,13,18-trioxo-3,14,17-trioxa-5,12-diazaicos-19-enyl methacrylate, 1,18-bis(cyclohexyloxy)-5,14-dioxo-4,15-dioxa-6,13-diazaoctadecane-2,17-diyl diacrylate, 1-(cyclohexyloxy)-17-(cyclohexyloxymethyl)-5,14,19-trioxo-4,15,18-trioxa-6,13-diazahenicos-20-en-2-yl methacrylate, 1,18-bis(cyclohexyloxy)-5,14-dioxo-4,15-dioxa-6,13-diazaoctadecane-2,17-diylbis(2-methylacrylate), 7,7,9-trimethyl-4,13-dioxo-3,14-dioxa-5,12-diazahexadecane-1,16-diylbis(2-methylacrylate), 7,7,9-trimethyl-4,13-dioxo-3,14-dioxa-5,12-diazahexadecane-1,16-diyl diacrylate, 2,2'-(1,3-phenylenebis(methylene))bis(azanediyl)bis(oxomethylene)bis(oxy)bis(ethane-2,1-diyl)bis(2-methacrylate), 2,2'-(1,3-phenylenebis(methylene))bis (azanediyl)bis(oxomethylene)bis(oxy)bis(ethane-2,1-diyl) diacrylate, 2-(3-(((2-(acryloyloxy)ethoxy)carbonylamino)methyl)benzylcarbamoyloxy)ethyl methacrylate, 2,2'-(1,3-phenylenebis(methylene))bis(methylazanediyl)bis (oxomethylene)bis(oxy)bis(ethane-2,1-diyl)bis(2-methacrylate), 2,2'-(1,3-phenylenebis(methylene))bis(methylazanediyl)bis(oxomethylene)bis(oxy)bis(ethane-2,1-diyl)diacrylate, 2-((3-((((2-(acryloyloxy)ethoxy)carbonyl)(methyl)amino)methyl)benzyl)(m ethyl)carbamoyloxy) ethyl methacrylate, 2,2'-(1,3-phenylenebis(methylene))bis(azanediyl)bis(oxomethylene)bis(oxy)bis(propane-2,1-diyl)bis(2-methylacrylate), 2,2'-(1,3-phenylenebis(methylene))bis(azanediyl)bis(oxomethylene)bis(oxy)bis(propane-2,1-diyl)diacrylate, 2-(3-(((2-(acryloyloxy)ethoxy)carbonylamino)methyl)benzylcarbamoyloxy) propyl methacrylate, 2-(3-(((1-(acryloyloxy)propan-2-yloxy)carbonylamino)methyl)benzylcarbamoyloxy)ethyl methacrylate, 4,4'-(1,3-phenylenebis(methylene))bis(azanediyl)bisoxomethylene)bis(oxy)bis(4,1-phenylene)bis(2-methylacrylate), 4,4'-(1,3-phenylenebis(methylene))bis(azanediyl)bis(oxomethylene)bis(oxy)bis(4,1-phenylene)diacrylate, 4-(3-(((4-(acryloxy)phenoxy)carbonylamino)methyl)benzylcarbamoyloxy)phenyl methacrylate, 4,4'-(1,3-phenylenebis(methylene))bis(azanediyl)bis(oxomethylene)bis(oxy)bis(butane-4,1-diyl)bis(2-methylacrylate), 4,4'-(1,3-phenylenebis(methylene))bis(azanediyl)bis(oxomethylene)bis(oxy)bis(butane-4,1-diyl)diacrylate, 4-(3-(((4-(acryloyloxy)butoxy)carbonylamino)methyl)benzylcarbamoyloxy)butyl methacrylate, 2,2'-(1,3-phenylenebis(methylene))bis(azanediyl)bis(oxomethylene) bis(oxy)bis(3-phenoxypropane-2,1-diyl)bis(2-methylacrylate), 2,2'-(1,3-phenylenebis(methylene))bis(azanediyl)bis(oxomethylene)bis(oxy)bis(3-phenoxypropane-2,1-diyl)diacrylate, 2-(3-(((1-(acryloyloxy)-3-phenoxypropan-2-yloxy)carbonylamino)methyl)benzylcarbamoyloxy)-3-phenoxypropyl methacrylate, 2-2'-(1,3-phenylenebis(methylene))bis(azanediyl)bis(oxomethylene)bis(oxy)bis(3-(phenylamino)propane-2,1-diyl)bis(2-methylacrylate), 2-2'-(1,3-phenylenebis(methylene))bis(azanediyl)bis(oxomethylene)bis(oxy)bis(3-(phenylamino)propane-2,1-diyl)diacrylate, 2-(3-(((1-(acryloyloxy)-3-(phenylamino)propan-2-yloxy)carbonylamino)methyl)benzylcarbamoyloxy)-3-(phenylamino)propyl methacrylate, 2,2'-(1,3-phenylenebis(methylene))bis(azanediyl)bis(oxomethylene)bis(oxy)bis(3-(phenylthio)propane-2,1-diyl)bis(2-methylacrylate), 2,2'-(1,3-phenylenebis(methylene))bis(azanediyl)bis(oxomethylene)bis(oxy)bis(3-(phenylthio)propane-2,1-diyl)diacrylate, 2-(3-(((1-(acryloxy)-3-(phenylthio)propan-2-yloxy)carbonylamino)methyl)benzylcarbamoyloxy)-3-(phenylthio)propyl methacrylate, 2,2'-(1,3-phenylenebis(methylene))bis(azanediyl)bis(oxomethylene)bis(oxy)bis(3-(benzyloxy)propane-2,1-diyl)bis(2-methylacrylate), 2,2'-(1,3-phenylenebis(methylene))bis(azanediyl)bis(oxomethylene)bis(oxy)bis(3-(benzyloxy)propane-2,1-diyl)diacrylate, 2-(3-(((1-(acryloyloxy)-3-(benzyloxy)propan-2-yloxy)carbonylamino)methyl)benzylcarbamoyloxy)-3-(benzyloxy)propyl methacrylate, 2,2'-(1,3-phenylenebis(methylene))bis(azanediyl)bis(oxomethylene)bis(oxy)bis(3-(methacryloyloxy)propane-2,1-diyl)dibenzoate, 2,2'-(1,3-phenylenebis(methylene))bis(azanediyl)bis(oxomethylene)bis(oxy)bis(3-(acryloyloxy)propane-2,1-diyl)dibenzoate, 2,2'-(1,3-phenylenebis(methylene))bis(azanediyl)bis(oxomethylene)bis(oxy)bis(3-(2-phenylacetoxy)propane-2,1-diyl)bis(2-methylacrylate), 2,2'-(1,3-phenylenebis(methylene))bis(azanediyl)bis(oxomethylene)bis(oxy)bis(3-(2-phenylacetoxy)propane-2,1-diyl)diacrylate, 2-(3-(((1-(acryloyloxy)-3-(2-phenylacetoxy)propan-2-yloxy)carbonylamino)methyl)benzylcarbamoyloxy)-3-(2-phenylacetoxy)propyl methacrylate, 2,2'-(2,2'-(1,3-phenylene)bis(propane-2.2-diyl))bis(azanediyl)bis (oxomethylene)bis(oxy)bis(ethane-2,1-diyl)bis(2-methacrylate), 2,2'-(2,2'-(1,3-phenylene)bis(propane-2,2-diyl))bis(azanediyl)bis(oxomethylene)bis(oxy)bis(ethane-2,1-diyl)diacrylate, 2-(2-(3-(2-((2-(acryloyloxy)ethoxy)carbonylamino)propan-2-yl)phenyl)propan-2-ylcarbamoyloxy)ethyl methacrylate, 2,2'-(2,2'-(1,3-phenylene)bis(propane-2,2-diyl))bis(methylazanediyl)bis(oxomethylene)bis(oxy)bis(ethane-2,1-diyl)bis(2-methacrylate), 2,2'-(2,2'-(1,3-phenylene)bis(propane-2,2-diyl))bis(methylazanediyl)bis(oxomethylene)bis(oxy)bis(ethane-2,1-diyl)diacrylate, 2-((2-(3-(2-(((2-(acryloyloxy)ethoxy)carbonyl)(methyl)amino-propan-2-yl)phenyl)propan-2-yl)(methyl)carbamoyloxy)ethyl methacrylate, 2,2'-(2,2'-(1,3-phenylene)bis(propane-2,2-diyl))bis(azanediyl)bis(oxomethylene)bis(oxy)bis(propane-2,1-diyl)bis(2-methylacrylate), 2,2'-(2,2'-(1,3-phenylene)bis(propane-2,2-diyl))bis(azanediyl)bis(oxomethylene)bis(oxy)bis(propane-2,1-diyl)diacrylate, 2-(2-(3-(2-((2-(acryloyloxy)ethoxy)carbonylamino)propan-2-yl)phenyl)propan-2-ylcarbamoyloxy)propyl methacrylate, 2-(2-(3-(2-((1-(acryloyloxy)propan-2-yloxy)carbonyl)amino)propan-2-yl)carbamoyloxy)ethyl methacrylate, 4,4'-(2,2'-(1,3-phenylene)bis(propane-2,2-diyl))bis(azanediyl)bis(oxomethylene)bis(oxy)bis(4,1-phenylene)bis(2-methylacrylate), 4,4'-(2,2'-(1,3-phenylene)bis(propane-2,2-diyl))bis(azanediyl)bis(oxomethylene)bis(oxy)bis(4,1-phenylene)diacrylate, 4-(2-(3-(2-((4-(acryloyloxy)phenoxy)carbonylamino)propan-2-yl)phenyl)propan-2-yl)carbamoyloxy)phenyl methacrylate, 4,4'-(2,2'-(1,3-phenylene)bis(propane-2,2-diyl))bis(azanediyl)bis(oxomethylene)bis(oxy)bis(butane-4,1-diyl)bis(2-methacrylate), 4,4'-(2,2'-(1,3-phenylene)bis(propane-2,2-diyl))bis(azanediyl)bis(oxomethylene)bis(oxy)bis(butane-4,1-diyl)diacrylate, 4-(2-(3-(2-((4-acryloyloxy)butoxy)carbonylamino)propan-2-yl)phenyl)propan-2-ylcarbamoyloxy)butyl methacrylate, 2,2'-(2,2'-(1,3-phenylene)bis(propane-2,2-diyl))bis(azanediyl)bis(oxomethylene)bis(oxy)bis(3-phenoxypropane-2,1-diyl)bis(2-methacrylate), 2,2'-(2,2'-(1,3-phenylene)bis(propane-2,2-diyl))bis(azanediyl)bis(oxomethylene)bis(oxy)bis(3-phenoxypropane-2,1-diyl)diacrylate, 2-(2-(3-(2-((1-(acryloyloxy)-3-phenoxypropan-2-yloxy)carbonylamino)propan-2-yl)phenyl)propan-2-ylcarbamoyllxy)-3-phenoxypropyl methacrylate, 2,2'-(2,2'-(1,3-phenylene)bis(propane-2,2-diyl))bis(azanediyl)bis(oxomethylene)bis(oxy)bis(3-(phenylamino)propane-2,1-diyl)bis(2-methacrylate), 2,2'-(2,2'-(1,3-phenylene)bis(propane-2,2-diyl))bis(azanediyl)bis(oxomethylene)bis(oxy)bis(3-(phenylamino)propane-2,1-diyl)diacrylate, 2-(2-(3-(2-((1-(acryloyloxy)-3-(phenylamino)propan-2-yloxy)carbonylamino)propan-2-yl)phenyl)propan-2-ylcarbamoyloxy)-3-(phenylamino)propyl methacrylate, 2,2'-(2,2'-(1,3-phenylene)bis(propane-2,2-diyl))bis(azanediyl)bis(oxomethylene)bis(oxy)bis(3-(phenylthio)propane-2,1-diyl)bis(2-methylacrylate), 2,2'-(2,2'-(1,3-phenylene)bis(propane-2,2-diyl))bis(azanediyl)bis(oxomethylene)bis(oxy)bis(3-(phenylthio)propane-2,1-diyl)diacrylate, 2-(2-(3-(2-((1-(acryloyloxy)-3-(phenylthio)propan-2-yloxy)carbonylamino)propan-2-yl)phenyl)propan-2-ylcarbamoyloxy)-3-(phenylthio)propyl methacrylate, 2-2'-(2,2'-(1,3-phenylene)bis(propane-2,2-diyl))bis(azanediyl)bis(oxomethylene)bis(3-(benzyloxy)propan-2,1-diyl)bis(2-methylacrylate), 2-2'-(2,2'-(1,3-phenylene)bis(propane-2,2-diyl))bis(azanediyl)bis (oxomethylene)bis(3-(benzyloxy)propane-2,1-diyl) diacrylate, 2-(2-(3-(2-((1-(acryloyloxy)-3-(benzyloxy) propan-2-yloxy)carbonylamino)propan-2-yl)phenyl) propan-2-ylcarbamoyloxy)-3-(benzyloxy)propyl methacrylate, 2,2'-(2,2'-(1,3-phenylene)bis(propane-2,2-diyl))bis(azanediyl)bis(oxomethylene)bis(oxy)bis(3-(methacryloyloxy)propane-2,1-diyl)dibenzoate, 2,2'-(2,2'-(1,3-phenylene)bis(propane-2,2-diyl))bis(azanediyl)bis (oxomethylene)bis(oxy)bis(3-(acryloyloxy)propane-2,1-diyl)dibenzoate, 2,2'-(2,2'-(1,3-phenylene)bis(propane-2,2-diyl))bis(azanediyl)bis(oxomethylene)bis(oxy)bis(3-(2-phenylacetoxy)propane-2,1-diyl)bis(2-methacrylate), 2,2'-(2,2'-(1,3-phenylene)bis(propane-2,2-diyl))bis(azanediyl) bis(oxomethylene)bis(oxy)bis(3-(2-phenylacetoxy) propane-2,1-diyl)diacrylate, 2-(2-(3-(2-((1-(acryloyloxy)-3-(2-phenylacetoxy)propan-2-yloxy)carbonylamino)propan-2-yl)phenyl)propan-2-ylcarbamoyloxy)-3-(2-phenylacetoxy)propyl methacrylate and the like.

The composition preferably comprises a radical polymerizable monomer having a benzene ring and/or a cyclohexane ring and an urethane bond in the molecular skeleton. Examples of the monomer include ((((propane-2,2-diylbis (4,1-phenylene))bis(azanedioyl))bis(carbonyl))bis(oxy))bis (ethane-2,1-diyl)bis(2-methylacrylate), ((((methylenebis(4, 1-phenylene))bis(azanedioyl))bis(carbonyl))bis(oxy))bis (ethane-2,1-diyl)bis(2-methylacrylate), ((((2-methyl-1,3-phenylene)bis(azanediyl))bis(carbonyl))bis(oxy))bis(ethane-2,1-diyl)bis(2-methylacrylate), ((((cyclohexane-1,3-diylbis(methylene))bis(azanediyl))bis(carbonyl))bis(oxy))bi s(ethane-2,1-diyl) diacrylate, ((((methylenebis(4,1-phenylene))bis(azanediyl))bis(carbonyl))bis((oxy))bis(ethane-2,1-diyl) diacrylate, ((((2-methyl-1,3-phenylene)bis (azanediyl))bis(carbonyl))bis(oxy))bis(ethane-2,1-diyl) diacrylate, ((((cyclohexane-1,3-diylbis(methylene))bis (azanediyl))bis(carbonyl))bis(oxy))bis(ethane-2,1-diyl) bis (2-methylacrylate) as described in [Chemical Formula 6].

[Chemical Formula 6]

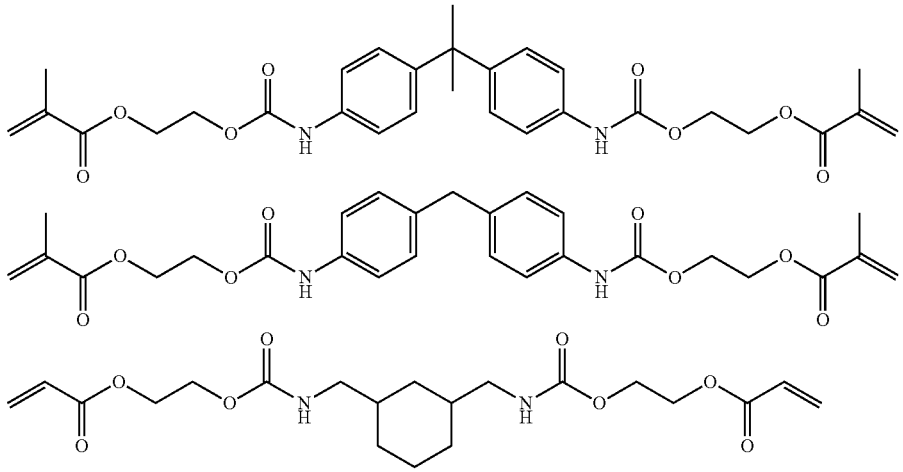

[Chemical Formula 7]

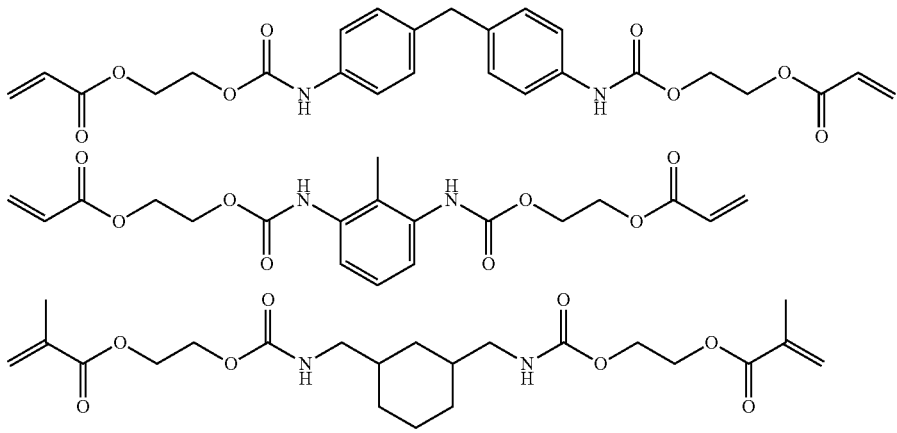

When the silane coupling agent of the embodiments of the present invention is applied to the medical and/or dental curable composition, it is preferable that at least one of a polymerization initiator and/or a polymerization accelerator is included. Regarding the preferable mixing amount, the mixing amount of the polymerization initiator and the polymerization accelerator is preferably 0.5% by weight to 5% by weight based on the radical polymerizable monomer. When the concentration is lower than 0.5% by weight, the mechanical strength decreases since many unpolymerized radical polymerizable monomers occur. When the concentration is higher than 5% by weight, the degree of polymerization decreases and the mechanical strength decreases.

As the polymerization initiator included in the medical and/or dental curable composition of the embodiments of the present invention, a polymerization initiator selected from a polymerization initiator that have been used in the industrial world can be used. Of these polymerization initiators, a polymerization initiator that has been used for medical and/or dental applications is preferably used. Particularly, a polymerization initiator for photopolymerization and chemical polymerization is used alone or as an appropriate combination of two or more. Specific examples of the photopolymerization initiator among the polymerization initiators included in the medical and/or dental curable composition of the embodiments of the present invention include (bis) acylphosphine oxides, water-soluble acylphosphine oxides, thioxanthones or quaternary ammonium salts of thioxanthones, ketals, α-diketones, coumarins, anthraquinones, benzoinalkyl ether compounds, α-amino ketone-based compounds and the like.

Specific examples of the acylphosphine oxides used as the photopolymerization initiator include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyldi-(2,6-dimethylphenyl)phosphonate and the like. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide and the like.

Specific examples of the thioxanthones or the quaternary ammonium salts of the thioxanthones used as the photopolymerization initiator include thioxanthone, 2-chlorothioxanthen-9-one, 2-hydroxy-3-(9-oxy-9H-thioxanthen-4-yloxy)-N,N,N-trimethyl-propane aluminum chloride, 2-hydroxy-3-(1-methyl-9-oxy-9H-thioxanthen-4-yloxy)-N,N,N-trimethyl-propane aluminum chloride, 2-hydroxy-3-(9-oxo-9H-thioxanthen-2-yloxy)-N,N,N-trimethyl-propane aluminum chloride, 2-hydroxy-3-(3,4-dimethyl-9-oxo-9H-thioxanthen-2-yloxy)-N,N,N-trimethyl-1-propane aluminum chloride, 2-hydroxy-3-(3,4-dimethyl-9H-thioxanthen-2-yloxy)-N,N,N-trimethyl-1-propane aluminum chloride, 2-hydroxy-3-(1,3,4-trimethyl-9-oxo-9H-thioxanthen-2-yloxy)-N,N,N-trimethyl-1-propane aluminum chloride and the like.

Specific examples of the α-diketones used as the photopolymerization initiator include diacetyl, dibenzyl, camphorquinone, 2,3-pentanedione, 2,3-octadione, 9,10-phenanthrenequinone, 4,4'-oxybenzyl, acenaphthenequinone and the like.

Specific examples of the coumarin compounds used as the photopolymerization initiator include compounds such as 3,3'-carbonylbis(7-diethylaminocoumarin), 3-(4-methoxybenzoyl)coumarin, 3-thenoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3-benzoyl-8-methoxycoumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl) coumarin, 3-benzoyl-8-methoxycoumarin, 3-benzoyl-6-nitrocoumarin-3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl) coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino) coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-1,1,7,7-tetramethyl1H,5H,11H-[1]benzopyrano[6,7,8-ij] quinolizin-11-one and 10-(2-benzothiazoyl)-2,3,6,7-tetrahydro-1,1,7,7-tetramethyl1H,5H,11H-[1]benzopyrano[6,7, 8-ij]quinolizin-11-one.

Of the coumarin compounds, particularly 3,3'-carbonylbis (7-diethylaminocoumarin) and 3,3'-carbonylbis(7-dibutylaminocoumarin) are suitable.

Specific examples of the anthraquinones used as the photopolymerization initiator include anthraquinone, 1-chloroanthraquinone, 2-chloroanthraquinone, 1-bromoanthraquinone, 1,2-benzanthraquinone, 1-methylanthraquinone, 2-ethylanthraquinone, 1-hydroxyanthraquinone and the like.

Specific examples of the benzoinalkyl ethers used as the photopolymerization initiator include benzoinmethyl ether, benzoinethyl ether, benzoinisopropyl ether, benzoinisobutyl ether and the like.

Specific examples of the α-amino ketones used as the photopolymerization initiator include 2-methyl-1-[4-(methylthio)phenyl]-2-morpholinopropan-1-one and the like.

Of the photopolymerization initiators, at least one selected from the group consisting of (bis)acylphosphine oxides and salts thereof, α-diketones and coumarin compounds is preferably used. As a result of this, a composition having excellent photocurability at visible and near-ultraviolet regions and that exhibits sufficient photocurability even when any light source of a halogen ramp, light-emitting diode (LED) and a xenon ramp is used.

As the chemical polymerization initiator among the polymerization initiators included in the medical and/or dental curable composition of the embodiments of the present invention, an organic peroxide is preferably used. The above-mentioned organic peroxide used in the chemical polymerization initiator is not particularly limited, and a known organic peroxide can be used. Examples of the representative organic peroxide include ketone peroxide, hydroperoxide, diacyl peroxide, dialkyl peroxide, peroxyketal, peroxy ester, peroxydicarbonate and the like.

Specific examples of the ketone peroxide used as the chemical polymerization initiator include methyl ethyl ketone peroxide, methyl isobutyl ketone peroxide, methylcyclohexanone peroxide and cyclohexanone peroxide and the like.

Specific examples of the hydroperoxide used as the chemical polymerization initiator include 2,5-dimethylhexane-2,5-dihydroperoxide, diisopropylbenzene hydroperoxide, cumene hydroperoxide, t-butyl hydroperoxide and 1,1,3,3-tetramethyl butyl hydroperoxide and the like.

Specific examples of the diacyl peroxide used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide and lauroyl peroxide and the like.

Specific examples of the dialkyl peroxide used as the chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene and 2,5-dimethyl-2,5-di(t-butylperoxy)-3-hexyne and the like.

Specific examples of the peroxyketal used as the chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane and 4,4-bis(t-butylperoxy)valeric acid-n-butyl ester and the like.

Specific examples of the peroxy ester used as the chemical polymerization initiator include α-cumylperoxyneodecanoate, t-butylperoxyneodecanoate, t-butylperoxypivalate, 2,2,4-trimethylpentylperoxy-2-ethylhexanoate, t-amylperoxy-2-ethylhexanoate, t-butylperoxy-2-ethylhexanoate, di-t-butylperoxyisophthalate, di-t-butylperoxyhexahydroterephthalate, t-butylperoxy-3,3,5-trimethylhexanoate, t-butylperoxyacetate, t-butylperoxybenzoate and t-butylperoxymaleic acid and the like.

Specific examples of the peroxydicarbonate used as the chemical polymerization initiator include di-3-methoxyperoxydicarbonate, di-2-ethylhexylperoxydicarbonate, bis(4-t-butylcyclohexyl)peroxydicarbonate, diisopropylperoxydicarbonate, di-n-propylperoxydicarbonate, di-2-ethoxyethylperoxydicarbonate and diallylperoxydicarbonate and the like.

Of the organic peroxides, diacyl peroxides are preferably used, and of the diacyl peroxides, benzoyl peroxides are particularly preferably used in terms of the comprehensive balance between safety, storage stability and radical formation ability.

Specific examples of the polymerization accelerator include amines, sulfinic acids and salts thereof, borate compounds, barbituric acid derivatives, triazine compounds, copper compounds, tin compounds, vanadium compounds, halogen compounds, aldehydes, thiol compounds and the like.

Amines used as the polymerization accelerator are divided into aliphatic amines and aromatic amines. Specific examples of the aliphatic amines include primary aliphatic amines such as n-butylamine, n-hexylamine and n-octylamine, secondary aliphatic amines such as diisopropylamine, dibutylamine and N-methyldiethanolamine, tertiary aliphatic amines such as N-methylethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine and tributylamine and the like. Of these amines, tertiary aliphatic amines are preferable, and of these tertiary aliphatic amines, N-methyldiethanolamine and triethanolamine are more preferably used in terms of the curability and the storage stability of the composition.

Specific examples of the aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid-n-butoxyethyl ester, 4-N,N-dimethylaminobenzoic acid-2-(methacryloyloxy)ethyl ester, 4-N,N-dimethylaminobenzophenone, 4-dimethylaminobenzoic acid butyl and the like. Of these aromatic amines, N,N-di(2-hydroxyethyl)-p-toluidine, 4-N,N-dimethylaminobenzoic acid ethyl ester, N,N-dimethylaminobenzoic acid-n-butoxyethyl ester and 4-N,N-dimethylaminobenzophenone and the like are exemplified in terms of capable of imparting excellent curability to the composition.

Specific examples of the sulfinic acids and salts thereof used as the polymerization accelerator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, calcium 2,4,6-triisopropylbenzenesulfinate and the like, and benzenesulfinate sodium, p-toluenesulfinate sodium and 2,4,6-triisopropylbenzenesulfinate sodium are particularly preferable.

Regarding the borate compounds used as the polymerization accelerator, specific examples of the borate compounds having one aryl group in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts and the like of trialkylphenylboron, trialkyl(p-chlorophenyl)boron, trialkyl(p-phlorophenyl)boron, trialkyl(3,5-bistriphloromethyl)phenylboron, trialkyl[3,5-bis(1,1,1,3,3,3-hexaphloro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron and trialkyl(m-octyloxyphenyl)boron (the alkyl group is at least one selected from the group consisting of an n-butyl group, an n-octyl group and an n-dodecyl group and the like).

Specific examples of the borate compounds having two aryl groups in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts and the like of dialkyldiphenylboron, dialkyldi(p-chlorophenyl)boron, dialkyldi(p-phlorophenyl)boron, dialkyldi(3,5-bistriphloromethyl)phenylboron, dialkyldi[3,5-bis(1,1,1,3,3,3-hexaphloro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron and dialkyldi(m-octyloxyphenyl)boron (the alkyl group is at least one selected from the group consisting of an n-butyl group, an n-octyl group and an n-dodecyl group and the like).

Furthermore, specific examples of the borate compounds having three aryl groups in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts and the like of monoalkyltriphenylboron, monoalkyltri(p-chlorophenyl)boron, monoalkyltri(p-phlorophenyl)boron, monoalkyltri(3,5-bistriphloromethyl)phenylboron, monoalkyltri[3,5-bis(1,1,1,3,3,3-hexaphloro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron and monoalkyltri(m-octyloxyphenyl)boron (the alkyl group is at least one selected from an n-butyl group, an n-octyl group or an n-dodecyl group or the like).

Furthermore, specific examples of the borate compounds having four aryl groups in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts and the like of tetraphenylboron, tetrakis(p-chlorophenyl)boron, tetrakis(p-phlorophenyl)boron, tetrakis(3,5-bistriphloromethyl)phenylboron, tetrakis[3,5-bis(1,1,1,3,3,3-hexaphloro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-phlorophenyl)triphenylboron, (3,5-bistriphloromethyl)phenyltriphenylboron, (p-nitrophenyl)triphenylboron, (m-butyloxyphenyl)triphenylboron, (p-butyloxyphenyl)triphenylboron, (m-octyloxyphenyl)triphenylboron and (p-octyloxyphenyl)triphenylboron.

Of these arylborate compounds, borate compounds having three or four aryl groups in one molecule are preferably used in terms of storage stability. These arylborate compounds may be used as one or a mixture of two or more.

Specific examples of the barbituric acid derivatives used as the polymerization accelerator include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid and thiobarbituric acids, and salts thereof (particularly alkali metals or alkaline earth metals are preferable). Examples of the salts of these barbituric acids include sodium 5-butylbarbiturate, sodium 1,3,5-trimethylbarbiturate and sodium 1-cyclohexyl-5-ethylbarbiturate and the like.

Specific examples of particularly suitable barbituric acid derivatives include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acids and the like.

Specific examples of the triazine compounds used as the polymerization accelerator include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, 2-[2-{N,N-diallylamino}ethoxy]-4,6-bis(trichloromethyl)-s-triazine and the like.

Of the triazine compounds exemplified above, particularly preferable triazine compounds include 2,4,6-tris(trichloromethyl)-s-triazine in terms of polymerization activity and 2-phenyl-4,6-bis(trichloromethyl)-s-triazine, 2-(p-chlorophenyl)-4,6-bis(trichloromethyl)-s-triazine and 2-(4-biphenylyl)-4,6-bis(trichloromethyl)-s-triazine in terms of storage stability. The above-mentioned triazine compounds may be used as one or a mixture of two or more.

Specific examples of the copper compounds used as the polymerization accelerator include acetylacetone copper, cupric acetate, copper oleinate, cupric chloride, cupric bromide and the like.

Specific examples of the tin compounds used as the polymerization accelerator include di-n-butyltin dimaleate, di-n-octyltin dimaleate, di-n-octyltin dilaurate, di-n-butyltin dilaurate and the like. Particularly suitable tin compounds include di-n-octyltin dilaurate and di-n-butyltin dilaurate.

The vanadium compounds used as the polymerization accelerator are preferably tetravalent and/or pentavalent vanadium compounds. Specific examples of the tetravalent and/or pentavalent vanadium compounds include vanadium (IV) oxide, vanadium(IV) oxide acetylacetonate, vanadyl (IV) oxalate, vanadyl(IV) sulfate, oxobis(1-phenyl-1,3-butanedionate)vanadium(IV), bis(maltolato)oxovanadium (IV), vanadium(V) oxide, sodium metavanadate(V), ammonium metavanadate(V) and the like.

Specific examples of the halogen compounds used as the polymerization accelerator include dilauryldimethylammonium chloride, lauryldimethylbenzylammonium chloride, benzyltrimethylammonium chloride, tetramethylammonium chloride, benzyldimethylcetylammonium chloride, dilauryldimethylammonium bromide and the like.

Specific examples of the aldehydes used as the polymerization accelerator include terephthalaldehyde and benzaldehyde derivatives and the like. Examples of the benzaldehyde derivatives include dimethylaminobenzaldehyde, p-methyloxybenzaldehyde, p-ethyloxybenzaldehyde, p-n-octyloxybenzaldehyde and the like. Of these benzaldehyde derivatives, p-n-octyloxybenzaldehyde is preferably used in terms of curability.

Specific examples of the thiol compounds used as the polymerization accelerator include 3-mercaptopropyltrimethoxysilane, 2-mercaptobenzooxazole, decanethiol, thiobenzoic acid and the like.

Components that can be included in the medical and/or dental curable composition of the embodiments of the present invention is optional, and specific examples thereof include colorants such as dyes and pigments, thickeners, aromatics and the like.

Example

A method for producing a silane coupling agent and a method for preparing a medical and/or dental curable composition comprising the same of the present invention, and physical properties will be described in detail below, but the present invention is in no way limited to the description thereof.

an oil bath for 24 hours, leading to aging. After completion of the aging, the four-necked flask was removed from the oil bath and the reaction product was returned to room temperature, and then HPLC and FT-IR measurements were performed. For preparing the sample, a very small amount was pipetted off and the solvent was removed with an evaporator. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, the raw materials 1,6-diisocyanate-hexane and 2-hydroxyethyl methacrylate disappeared and a new peak of 2-(((6-isocyanate-hexyl) carbamoyl)oxy)ethyl methacrylate (molecular weight 298.34) was confirmed. As a result of FT-IR measurement, a decrease in isocyanate absorption intensity at 2280-2250 $cm^{-1}$ and a disappearance of hydroxy group absorption near 3300 $cm^{-1}$ were confirmed, and a new absorption attributed to urethane group at 1250 $cm^{-1}$ was confirmed. Next, to a toluene solution containing 29.8 g (0.10 mol) of the precursor compound synthesized in the above procedure, 18.0 g (0.10 mol) of 3-(trimethoxysilyl)propan-1-ol was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, the peaks of the raw materials 2-(((6-isocyanate-hexyl)carbamoyl)oxy)ethyl methacrylate and 3-(trimethoxysilyl)propan-1-ol disappeared and a new peak of 3,3-dimethoxy-8,17-dioxo-2,7,18-trioxa-9,16-diaza-3-silicosan-20-yl methacrylate (molecular weight 478.61) was confirmed. As a result of FT-IR measurement, a disappearance of isocyanate absorption at 2280-2250 $cm^{-1}$ and a disappearance of hydroxy group absorption near 3300 $cm^{-1}$ were confirmed. The chemical structure formula of the compound synthesized in this synthetic example are described below.

[Chemical Formula 8]

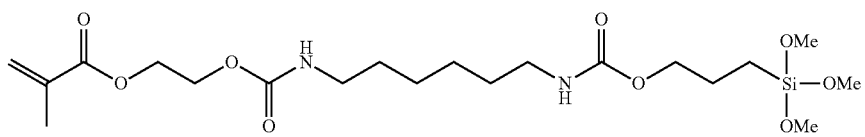

(Synthesis Example 11) Synthesis of Silane Coupling Agent with Radical Polymerizable Group 11

To a four-necked flask (1 L volume) equipped with stirring blades, a thermometer, a dropping funnel and a condenser tube, 300 mL of toluene, 16.8 g (0.10 mol) of 1,6-diisocyanate hexane, and 47.9 mg of p-methoxyphenol were added and dissolved. Next, 13.0 g (0.1 mol) of 2-hydroxyethyl methacrylate was weighed in a beaker, 150 mL of toluene was added, and the mixture was stirred thoroughly and transferred to a dropping funnel. The four-necked flask was immersed in an oil bath heated to 80° C., and 2-hydroxyethyl methacrylate was added dropwise with stirring. After completion of the dropwise addition, the reaction was continued while maintaining the temperature of (Synthesis Example 12) Synthesis of Silane Coupling Agent with Radical Polymerizable Group 12

To a four-necked flask (1 L volume) equipped with stirring blades, a thermometer, a dropping funnel and a condenser tube, 300 mL of toluene, 16.8 g (0.10 mol) of 1,6-diisocyanate hexane, and 52.3 mg of p-methoxyphenol were added and dissolved. Next, 17.4 g (0.1 mol) of 2-(2-hydroxyethoxy)ethyl methacrylate was weighed in a beaker, 150 mL of toluene was added, and the mixture was stirred thoroughly and transferred to a dropping funnel. The four-necked flask was immersed in an oil bath heated to 80° C., and 2-(2-hydroxyethoxy)ethyl methacrylate was added dropwise with stirring. After completion of the dropwise addition, the reaction was continued while maintaining the temperature of an oil bath for 24 hours, leading to aging. After completion of the aging, the four-necked flask was removed from the oil bath and the reaction product was returned to room temperature, and then HPLC and FT-IR measurements were performed. For preparing the sample, a very small amount was pipetted off and the solvent was removed with an evaporator. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, the raw materials 1,6-diisocyanate-hexane and 2-(2-hydroxyethoxy)ethyl methacrylate disappeared and a new peak of 2-(2-(((6-isocyanate-hexyl)carbamoyl)oxy)ethoxy)ethyl methacrylate (molecular weight 342.39) was confirmed. As a result of FT-IR measurement, a decrease in isocyanate absorption intensity at 2280-2250 $cm^{-1}$ and a disappearance of hydroxy group absorption near 3300 $cm^{-1}$ were confirmed, and a new absorption attributed to urethane group at 1250 $cm^{-1}$ was confirmed. Next, to a toluene solution containing 34.2 g (0.10 mol) of the precursor compound synthesized in the above procedure, 18.0 g (0.10 mol) of 3-(trimethoxysilyl)propan-1-ol was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, the peaks of the raw materials 2-(2-(((6-isocyanate-hexyl)carbamoyl)oxy)ethoxy)ethyl methacrylate and 3-(trimethoxysilyl)propan-1-ol disappeared and a new peak of 3,3-dimethoxy-8,17-dioxo-2,7,18,21-tetraoxa-9,16-diaza-3-silatricosan-23-yl methacrylate (molecular weight 522.67) was confirmed. As a result of FT-IR measurement, a disappearance of isocyanate absorption at 2280-2250 $cm^{-1}$ and a disappearance of hydroxy group absorption near 3300 $cm^{-1}$ were confirmed. The chemical structure formula of the compound synthesized in this synthetic example are described below.

were added and dissolved. Next, 17.2 g (0.1 mol) of 5-hydroxypentyl methacrylate was weighed in a beaker, 150 mL of toluene was added, and the mixture was stirred thoroughly and transferred to a dropping funnel. The four-necked flask was immersed in an oil bath heated to 80° C., and 5-hydroxypentyl methacrylate was added dropwise with stirring. After completion of the dropwise addition, the reaction was continued while maintaining the temperature of an oil bath for 24 hours, leading to aging. After completion of the aging, the four-necked flask was removed from the oil bath and the reaction product was returned to room temperature, and then HPLC and FT-IR measurements were performed. For preparing the sample, a very small amount was pipetted off and the solvent was removed with an evaporator. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, the raw materials 1,6-diisocyanate-hexane and 5-hydroxypentyl methacrylate disappeared and a new peak of 5-(((6-isocyanate-hexyl)carbamoyl)oxy)pentyl methacrylate (molecular weight 340.42) was confirmed. As a result of FT-IR measurement, a decrease in isocyanate absorption intensity at 2280-2250 $cm^{-1}$ and a disappearance of hydroxy group absorption near 3300 $cm^{-1}$ were confirmed, and a new absorption attributed to urethane group at 1250 $cm^{-1}$ was confirmed. Next, to a toluene solution containing 34.0 g (0.10 mol) of the precursor compound synthesized in the above procedure, 18.0 g (0.10 mol) of 3-(trimethoxysilyl)propan-1-ol was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, peaks of the raw materials 5-(((6-isocyanate-hexyl)carbamoyl)oxy)pentyl methacrylate and 3-(trimethoxysilyl)propan-1-ol disappeared and a new peak

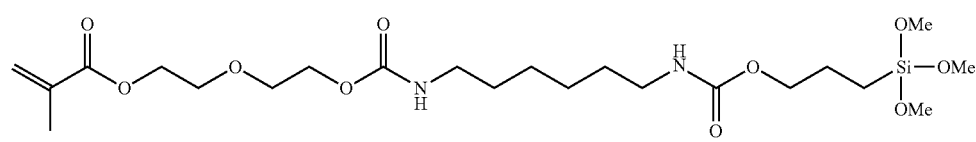

[Chemical Formula 9]

(Synthesis Example 13) Synthesis of Silane Coupling Agent with Radical Polymerizable Group 13

To a four-necked flask (1 L volume) equipped with stirring blades, a thermometer, a dropping funnel and a condenser tube, 300 mL of toluene, 16.8 g (0.10 mol) of 1,6-diisocyanate hexane, and 52.1 mg of p-methoxyphenol of 3,3-dimethoxy-8,17-dioxo-2,7,18-trioxa-9,16-diaza-3-silatricosan-23-yl methacrylate (molecular weight 520.70) was confirmed. As a result of FT-IR measurement, a disappearance of isocyanate absorption at 2280-2250 $cm^{-1}$ and a disappearance of hydroxy group absorption near 3300 $cm^{-1}$ were confirmed. The chemical structure formula of the compound synthesized in this synthetic example are described below.

[Chemical Formula 10]

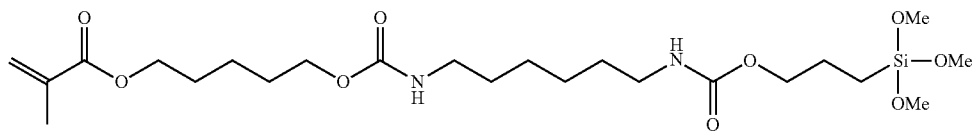

(Synthesis Example 14) Synthesis of Silane Coupling Agent with Radical Polymerizable Group 14

To a four-necked flask (1 L volume) equipped with stirring blades, a thermometer, a dropping funnel and a condenser tube, 300 mL of toluene, 15.4 g (0.10 mol) of 1,5-diisocyanate pentane, and 46.5 mg of p-methoxyphenol were added and dissolved. Next, 13.0 g (0.1 mol) of 2-hydroxyethyl methacrylate was weighed in a beaker, 150 mL of toluene was added, and the mixture was stirred thoroughly and transferred to a dropping funnel. The four-necked flask was immersed in an oil bath heated to 80° C., and 2-hydroxyethyl methacrylate was added dropwise with stirring. After completion of the dropwise addition, the reaction was continued while maintaining the temperature of an oil bath for 24 hours, leading to aging. After completion of the aging, the four-necked flask was removed from the oil bath and the reaction product was returned to room temperature, and then HPLC and FT-IR measurements were performed. For preparing the sample, a very small amount was pipetted off and the solvent was removed with an evaporator. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, the raw materials 1,5-diisocyanate pentane and 2-hydroxyethyl methacrylate disappeared and a new peak of 2-(((5-isocyanate-pentyl)carbamoyl)oxy)ethyl methacrylate (molecular weight 284.31) was confirmed. As a result of FT-IR measurement, a decrease in isocyanate absorption intensity at 2280-2250 $cm^{-1}$ and a disappearance of hydroxy group absorption near 3300 $cm^{-1}$ were confirmed, and a new absorption attributed to urethane group at 1250 $cm^{-1}$ was confirmed. Next, to a toluene solution containing 28.4 g (0.10 mol) of the precursor compound synthesized in the above procedure, 18.0 g (0.10 mol) of 3-(trimethoxysilyl)propan-1-01 was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, the peaks of the raw materials 2-(((5-isocyanate-pentyl)carbamoyl)oxy)ethyl methacrylate and 3-(trimethoxysilyl)propan-1-ol disappeared and 3,3-dimethoxy-8,16-dioxo-2,7,17-trioxa-9,15-diaza-3-silanonadecan-19-yl methacrylate (molecular weight 464.59) was confirmed. As a result of FT-IR measurement, a disappearance of isocyanate absorption at 2280-2250 $cm^{-1}$ and a disappearance of hydroxy group absorption near 3300 $cm^{-1}$ were confirmed. The chemical structure formula of the compound synthesized in this synthetic example are described below.

[Chemical Formula 11]

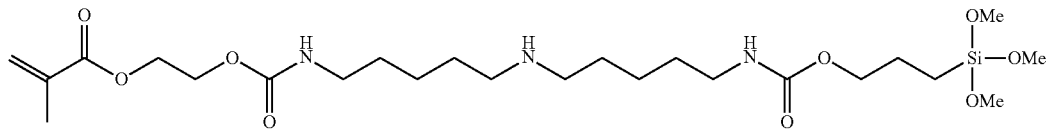

(Synthesis Example 15) Synthesis of Silane Coupling Agent with Radical Polymerizable Group 15

To a four-necked flask (1 L volume) equipped with stirring blades, a thermometer, a dropping funnel and a condenser tube, 300 mL of toluene, 12.6 g (0.10 mol) of 1,2-diisocyanate propan, and 43.7 mg of p-methoxyphenol were added and dissolved. Next, 13.0 g (0.1 mol) of 2-hydroxyethyl methacrylate was weighed in a beaker, 150 mL of toluene was added, and the mixture was stirred thoroughly and transferred to a dropping funnel. The four-necked flask was immersed in an oil bath heated to 80° C., and 2-hydroxyethyl methacrylate was added dropwise with stirring.

After completion of the dropwise addition, the reaction was continued while maintaining the temperature of an oil bath for 24 hours, leading to aging. After completion of the aging, the four-necked flask was removed from the oil bath and the reaction product was returned to room temperature, and then HPLC and FT-IR measurements were performed. For preparing the sample, a very small amount was pipetted off and the solvent was removed with an evaporator. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, the raw materials 1,2-diisocyanate propan and 2-hydroxyethyl methacrylate disappeared and a new peak of 2-(((1-isocyanate-propan-2-yl)carbamoyl)oxy)ethyl methacrylate (molecular weight 256.26) was confirmed. As a result of FT-IR measurement, a decrease in isocyanate absorption intensity at 2280-2250 $cm^{-1}$ and a disappearance of hydroxy group absorption near 3300 $cm^{-1}$ were confirmed, and a new absorption attributed to urethane group at 1250 $cm^{-1}$ was confirmed. Next, to a toluene solution containing 25.6 g (0.10 mol) of the precursor compound synthesized in the above procedure, 18.0 g (0.10 mol) of 3-(trimethoxysilyl)propan-1-ol was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, the peaks of the raw materials 2-(((1-isocyanate-propan-2-yl)carbamoyl)oxy)ethyl methacrylate and 3-(trimethoxysilyl)propan-1-ol disappeared and 3,3-dimethoxy-11-methyl-8,13-dioxo-2,7,14-trioxa-9,12-diaza-3-silahexadecan-16-yl methacrylate (molecular weight 436.53) was confirmed. As a result of FT-IR measurement, a disappearance of isocyanate absorption at 2280-2250 cm$^{-1}$ and a disappearance of hydroxy group absorption near 3300 cm$^{-1}$ were confirmed. The chemical structure formula of the compound synthesized in this synthetic example are described below.

[Chemical Formula 12]

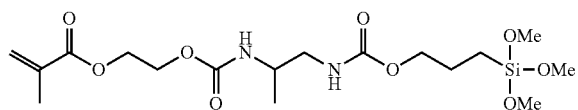

at around 3,300 cm$^{-1}$ was confirmed, and the absorption attributed to a urethane group was newly confirmed at 1,250 cm$^{-1}$. Next, to a four-necked flask containing 32.5 g (0.10 mol) of the compound synthesized by the above-mentioned operation, 4.9 mg (corresponding to 100 ppm) of platinum (0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 2-((10-undecenyloxy)carbonylamino)ethyl methacrylate and triethoxysilane as raw materials disappeared, and new peak of 4,4-diethoxy-17-oxo-3,16-dioxa-18-aza-4-silaicosan-20-yl methacrylate (molecular weight of 489.7) was confirmed. As a result of the FT-IR measurement, the disappearance of the silane group absorption at 2,190 cm$^{-1}$ was confirmed. The chemical structure of the compound synthesized in the present Synthesis Example is mentioned below.

[Chemical Formula 13]

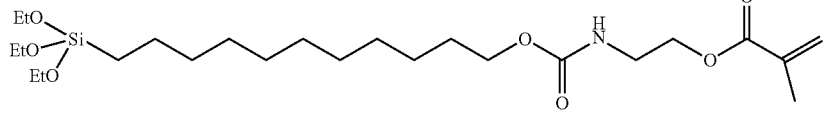

(Comparative Synthesis Example 11) Comparative Synthesis of Silane Coupling Agent 1 Having a Radical Polymerizable Group In a four-necked flask (volume of 100 mL) equipped with stirring blades, a thermometer, a dropping funnel and a condenser tube, 17.0 g (0.10 mol) of 10-undecen-1-ol, and 16.3 mg (corresponding to 500 ppm) of p-methoxyphenol were charged and dissolved. Subsequently, 15.5 g (0.10 mol) of 2-isocyanatoethyl methacrylate was weighed in the dropping funnel. The four-necked flask was immersed in an oil bath heated to 75° C., and 2-isocyanatoethyl methacrylate was added dropwise while stirring so that the inner temperature did not exceed 80° C. After completion of the dropwise addition, the reaction was continued while maintaining the temperature of an oil bath for 12 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, raw materials 10-undecen-1-ol and 2-isocyanatoethyl methacrylate disappeared, and new peak of 2-((10-undecenyloxy)carbonylamino)ethyl methacrylate (molecular weight of 325.4) was confirmed. As a result of the FT-IR measurement, the isocyanate absorption at 2,280 to 2,250 cm$^{-1}$ and the disappearance of the hydroxy group absorption Examples 11-1 to 11-5

(Preparation of Medical and/or Dental Composite Resins—Inorganic Matter Filling Rate of 70% by Weight)

Using polymerizable silane coupling agents synthesized in Synthesis Examples 11 to 15, surface modification with OX-(manufactured by NIPPON AEROSIL CO., LTD.) and Fuselex (manufactured by TATSUMORI LTD.) and preparation of medical and/or dental composite resins were performed. Specific surface modification method will be mentioned below. Each synthesized silane coupling agent in the amount mentioned in Tables 11-1 was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 11-1 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

Examples 12-1 to 12-5

(Preparation of Medical and/or Dental Composite Resins—Inorganic Matter Filling Rate of 85% by Weight)

Using polymerizable silane coupling agents synthesized in Synthesis Examples 11 to 15, surface modification with OX-(manufactured by NIPPON AEROSIL CO., LTD.) and Fuselex (manufactured by TATSUMORI LTD.) and preparation of medical and/or dental composite resins were performed. Specific surface modification method will be mentioned below. Each synthesized silane coupling agent in the amount mentioned in Tables 11-2 was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 11-2 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

Comparative Examples 11-1 to 11-3

(Preparation of Medical and/or Dental Composite Resins—Inorganic Matter Filling Rate of 70% by Weight)

Using a commercially available polymerizable silane coupling agent and the silane coupling agent synthesized in Comparative Synthesis Example 11, surface modification with OX-50 (manufactured by NIPPON AEROSIL CO., LTD.) and Fuselex (manufactured by TATSUMORI LTD.) and preparation of medical and/or dental composite resins were performed. Specific surface modification method will be mentioned below. Each silane coupling agent in the amount mentioned in Tables 11-1 was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 11-1 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

Comparative Examples 12-1 to 12-3

(Preparation of Medical and/or Dental Composite Resins—Inorganic Matter Filling Rate of 85% by Weight)

Using a commercially available polymerizable silane coupling agent and the silane coupling agent synthesized in Comparative Synthesis Example 11, surface modification with OX-50 (manufactured by NIPPON AEROSIL CO., LTD.) and Fuselex (manufactured by TATSUMORI LTD.) and preparation of medical and/or dental composite resins were performed. Specific surface modification method will be mentioned below. Each a commercially available silane coupling agent in the amount mentioned in Tables 11-2 was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 11-2 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

(Synthesis Example 21) Synthesis of Silane Coupling Agent with Radical Polymerizable Group 21

To a four-necked flask (1 L volume) equipped with stirring blades, a thermometer, a dropping funnel and a condenser tube, 500 mL of toluene, 27.5 g (0.11 mol) of bis(4-isocyanate-phenyl)methane, and 60.3 mg of p-methoxyphenol were added and dissolved. Next, 14.3 g (0.11 mol) of 2-hydroxyethyl methacrylate was weighed in a beaker, 150 mL of toluene was added, and the mixture was stirred thoroughly and transferred to a dropping funnel. The four-necked flask was immersed in an oil bath heated to 80° C., and 2-hydroxyethyl methacrylate was added dropwise with stirring. After completion of the dropwise addition, the reaction was continued while maintaining the temperature of an oil bath for 24 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, the raw materials bis(4-isocyanate-phenyl)methane and 2-hydroxyethyl methacrylate disappeared and a new peak of 2-(((4-(4-isocyanate-benzyl)phenyl)carbamoyl)oxy)ethyl methacrylate (molecular weight 380.4) was confirmed. As a result of FT-IR measurement, a decrease in isocyanate absorption intensity at 2280-2250 $cm^{-1}$ and a disappearance of hydroxy group absorption near 3300 $cm^{-1}$ were confirmed, and a new absorption attributed to urethane group at 1250 $cm^{-1}$ was confirmed. Next, to a toluene solution containing 38.0 g (0.10 mol) of the precursor compound synthesized in the above procedure, 22.2 g (0.10 mol) of 3-(triethoxysilyl)propan-1-ol was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, the peaks of the raw materials 2-(((4-(4-isocyanate-benzyl)phenyl)carbamoyl)oxy)ethyl methacrylate and 3-(triethoxysilyl)propan-1-ol disappeared and 2-(((4-(4-(((3-(triethoxysilyl)propoxy)carbonyl)amino)benzyl)phenyl)carbamoyl)oxy)ethyl methacrylate (molecular weight 602.76) was confirmed. As a result of FT-IR measurement, a disappearance of isocyanate absorption at 2280-2250 cm$^{-1}$ and a disappearance of hydroxy group absorption near 3300 cm$^{-1}$ were confirmed. The chemical structure formula of the compound synthesized in this synthetic example are described below.

an ATR method. As a result of the HPLC measurement, the raw materials 4,4'-(propane-2,2-diyl)bis(isocyanate-benzene) and 2-hydroxyethyl methacrylate disappeared and a new peak of 2-(((4-(2-(4-isocyanate-phenyl)propane-2-yl)phenyl)carbamoyl)oxy)ethyl methacrylate (molecular weight 408.45) was confirmed. As a result of FT-IR measurement, a decrease in isocyanate absorption intensity at 2280-2250 cm$^{-1}$ and a disappearance of hydroxy group absorption near 3300 cm$^{-1}$ were confirmed, and a new absorption attributed to urethane group at 1250 cm$^{-1}$ was confirmed. Next, to a toluene solution containing 40.8 g (0.10 mol) of the precursor compound synthesized in the above procedure, 22.2 g (0.10 mol) of 3-(triethoxysilyl)propan-1-ol was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, the peaks of the raw materials

[Chemical Formula 14]

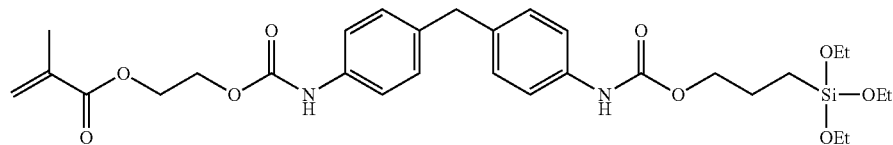

(Synthesis Example 22) Synthesis of Silane Coupling Agent with Radical Polymerizable Group 22

To a four-necked flask (1 L volume) equipped with stirring blades, a thermometer, a dropping funnel and a condenser tube, 500 mL of toluene, 30.6 g (0.11 mol) of 4,4'-(propane-2,2-diyl)bis(isocyanate-benzene), and 63.1 mg of p-methoxyphenol were added and dissolved. Next, 14.3 g (0.11 mol) of 2-hydroxyethyl methacrylate was weighed in a beaker, 150 mL of toluene was added, and the mixture was stirred thoroughly and transferred to a dropping funnel. The four-necked flask was immersed in an oil bath heated to 80° C., and 2-hydroxyethyl methacrylate was added dropwise with stirring. After completion of the dropwise addition, the reaction was continued while maintaining the temperature of an oil bath for 24 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by 2-(((4-(2-(4-isocyanate-phenyl)propane-2-yl)phenyl)carbamoyl)oxy)ethyl methacrylate and 3-(triethoxysilyl)propan-1-ol disappeared and 2-(((4-(2-(4-(((3-(triethoxysilyl)propoxy)carbonyl)amino)phenyl)propan-2-yl)phenyl)carbamoyl)oxy)ethyl methacrylate (molecular weight 630.81) was confirmed. As a result of FT-IR measurement, a disappearance of isocyanate absorption at 2280-2250 cm$^{-1}$ and a disappearance of hydroxy group absorption near 3300 cm$^{-1}$ were confirmed. The chemical structure formula of the compound synthesized in this synthetic example are described below.

[Chemical Formula 15]

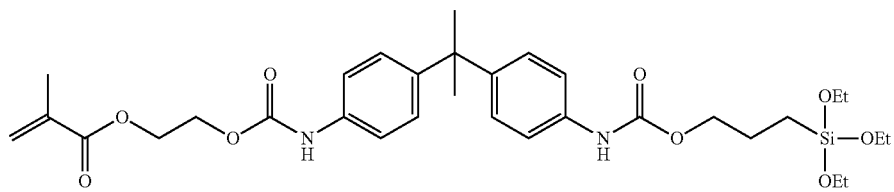

(Synthesis Example 23) Synthesis of Silane Coupling Agent with Radical Polymerizable Group 23

To a four-necked flask (1 L volume) equipped with stirring blades, a thermometer, a dropping funnel and a condenser tube, 500 mL of toluene, 19.2 g (0.11 mol) of 1,3-diisocyanate-2-methylbenzene, and 52.7 mg of p-methoxyphenol were added and dissolved. Next, 14.3 g (0.11 mol) of 2-hydroxyethyl methacrylate was weighed in a beaker, 150 mL of toluene was added, and the mixture was stirred thoroughly and transferred to a dropping funnel. The four-necked flask was immersed in an oil bath heated to 80°

C., and 2-hydroxyethyl methacrylate was added dropwise with stirring. After completion of the dropwise addition, the reaction was continued while maintaining the temperature of an oil bath for 24 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, the raw materials 1,3-diisocyanate-2-methylbenzene and 2-hydroxyethyl methacrylate disappeared and a new peak of 2-(((3-isocyanate-2-methylphenyl)carbamoyl)oxy)ethyl methacrylate (molecular weight 304.3) was confirmed. As a result of FT-IR measurement, a decrease in isocyanate absorption intensity at 2280-2250 cm$^{-1}$ and a disappearance of hydroxy group absorption near 3300 cm$^{-1}$ were confirmed, and a new absorption attributed to urethane group at 1250 cm$^{-1}$ was confirmed. Next, to a toluene solution containing 30.4 g (0.10 mol) of the precursor compound synthesized in the above procedure, 22.2 g (0.10 mol) of 3-(triethoxysilyl)propan-1-ol was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, the peaks of the raw materials 2-(((3-isocyanate-2-methylphenyl)carbamoyl)oxy)ethyl methacrylate and 3-(triethoxysilyl)propan-1-ol disappeared and 2-(((2-methyl-3-(((3-(triethoxysilyl)propoxy)carbonyl)amino)phenyl) carbamoyl)oxy)ethyl methacrylate (molecular weight 526.66) was confirmed. As a result of FT-IR measurement, a disappearance of isocyanate absorption at 2280-2250 cm$^{-1}$ and a disappearance of hydroxy group absorption near 3300 cm$^{-1}$ were confirmed. The chemical structure formula of the compound synthesized in this synthetic example are described below.

[Chemical Formula 16]

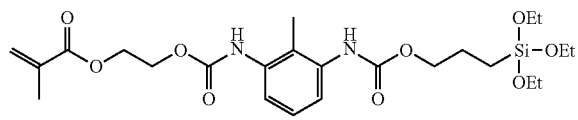

condenser tube, 500 mL of toluene, 21.4 g (0.11 mol) of 1,3-bis(isocyanate-methyl)cyclohexane, and 49.1 mg of p-methoxyphenol were added and dissolved. Next, 12.8 g (0.11 mol) of 2-hydroxyethyl acrylate was weighed in a beaker, 150 mL of toluene was added, and the mixture was stirred thoroughly and transferred to a dropping funnel. The four-necked flask was immersed in an oil bath heated to 80° C., and 2-hydroxyethyl acrylate was added dropwise with stirring. After completion of the dropwise addition, the reaction was continued while maintaining the temperature of an oil bath for 24 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, the raw materials 1,3-bis(isocyanate-methyl)cyclohexane and 2-hydroxyethyl acrylate disappeared and a new peak of 2-((((3-(isocyanate-methyl)cyclohexyl)methyl)carbamoyl)oxy)ethyl acrylate (molecular weight 310.35) was confirmed. As a result of FT-IR measurement, a decrease in isocyanate absorption intensity at 2280-2250 cm$^{-1}$ and a disappearance of hydroxy group absorption near 3300 cm$^{-1}$ were confirmed, and a new absorption attributed to urethane group at 1250 cm$^{-1}$ was confirmed. Next, to a toluene solution containing 31.0 g (0.10 mol) of the precursor compound synthesized in the above procedure, 22.2 g (0.10 mol) of 3-(triethoxysilyl)propan-1-ol was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, the peaks of the raw materials 2-((((3-(isocyanate-methyl)cyclohexyl)methyl)carbamoyl)oxy)ethyl acrylate and 3-(triethoxysilyl)propan-1-ol disappeared and 2-((((3-(3,3-dimethoxy-8-oxo-2,7-dioxa-9-aza-3-siladecan-10-yl)cyclohexyl)methyl)carbamoyl)oxy)ethyl acrylate (molecular weight 490.63) was confirmed. As a result of FT-IR measurement, a disappearance of isocyanate absorption at 2280-2250 cm$^{-1}$ and a disappearance of hydroxy group absorption near 3300 cm$^{-1}$ were confirmed. The chemical structure formula of the compound synthesized in this synthetic example are described below.

[Chemical Formula 17]

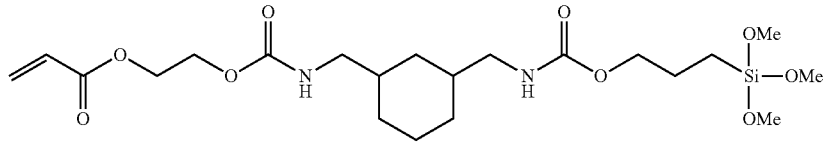

(Synthesis Example 24) Synthesis of Silane Coupling Agent with Radical Polymerizable Group 24

To a four-necked flask (1 L volume) equipped with stirring blades, a thermometer, a dropping funnel and a (Synthesis Example 25) Synthesis of Silane Coupling Agent with Radical Polymerizable Group 25

To a four-necked flask (1 L volume) equipped with stirring blades, a thermometer, a dropping funnel and a condenser tube, 500 mL of toluene, 19.2 g (0.11 mol) of 2,4-diisocyanate-1-methylbenzene, and 52.7 mg of p-methoxyphenol were added and dissolved. Next, 14.3 g (0.11 mol) of 2-hydroxyethyl methacrylate was weighed in a beaker, 150 mL of toluene was added, and the mixture was stirred thoroughly and transferred to a dropping funnel. The four-necked flask was immersed in an oil bath heated to 80° C., and 2-hydroxyethyl methacrylate was added dropwise with stirring. After completion of the dropwise addition, the reaction was continued while maintaining the temperature of an oil bath for 24 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, the raw materials 2,4-diisocyanate-1-methylbenzene and 2-hydroxyethyl methacrylate disappeared and a new peak of 2-(((5-isocyanate-2-methylphenyl)carbamoyl)oxy)ethyl methacrylate (molecular weight 304.30) was confirmed. As a result of FT-IR measurement, a decrease in isocyanate absorption intensity at 2280-2250 cm$^{-1}$ and a disappearance of hydroxy group absorption near 3300 cm$^{-1}$ were confirmed, and a new absorption attributed to urethane group at 1250 cm$^{-1}$ was confirmed. Next, to a toluene solution containing 30.4 g (0.10 mol) of the precursor compound synthesized in the above procedure, 22.2 g (0.10 mol) of 3-(triethoxysilyl)propan-1-ol was added dropwise with stirring. The reaction was performed with the immersion in an oil bath heated to 80° C. in the same way as in the first step. After completion of the dropwise addition, the reaction was continued for 24 hours, leading to aging. After completion of the aging, HPLC and FT-IR measurements were performed. As a result of the HPLC measurement, the peaks of the raw materials 2-(((5-isocyanate-2-methylphenyl)carbamoyl)oxy)ethyl methacrylate and 3-(triethoxysilyl)propan-1-ol disappeared and 2-(((2-methyl-5-(((3-(triethoxysilyl)propoxy)carbonyl)amino)phenyl) carbamoyl)oxy)ethyl methacrylate (molecular weight 526.66) was confirmed. As a result of FT-IR measurement, a disappearance of isocyanate absorption at 2280-2250 cm$^{-1}$ and a disappearance of hydroxy group absorption near 3300 cm$^{-1}$ were confirmed. The chemical structure formula of the compound synthesized in this synthetic example are described below.

[Chemical Formula 18]

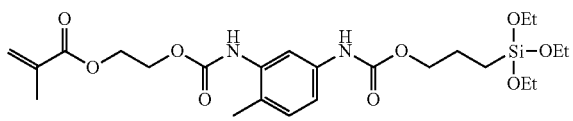

Examples 21-1 to 21-7

(Preparation of Medical and/or Dental Composite Resins)

Using polymerizable silane coupling agents synthesized in Synthesis Examples 21 to 25 and 11 to 12, surface modification with OX-50 (manufactured by NIPPON AEROSIL CO., LTD.) and Fuselex (manufactured by TATSUMORI LTD.) and preparation of medical and/or dental composite resins were performed. Specific surface modification method will be mentioned below. Each synthesized silane coupling agent in the amount mentioned in Tables 21-1 was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (Monomer-A, —C) and a photopolymerization initiator mentioned in Table 21-1 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins. The chemical structures of Monomer-A and —C are shown in [Chemical Formula 19].

Examples 22-1 to 22-7

(Preparation of Medical and/or Dental Composite Resins)

Using polymerizable silane coupling agents synthesized in Synthesis Examples 21 to 25 and 11 to 12, surface modification with OX-50 (manufactured by NIPPON AEROSIL CO., LTD.) and Fuselex (manufactured by TATSUMORI LTD.) and preparation of medical and/or dental composite resins were performed. Specific surface modification method will be mentioned below. Each synthesized silane coupling agent in the amount mentioned in Tables 21-2 was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (Monomer-B, -C) and a photopolymerization initiator mentioned in Table 21-2 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins. The chemical structures of Monomer-B and -C are shown in [Chemical Formula 19].

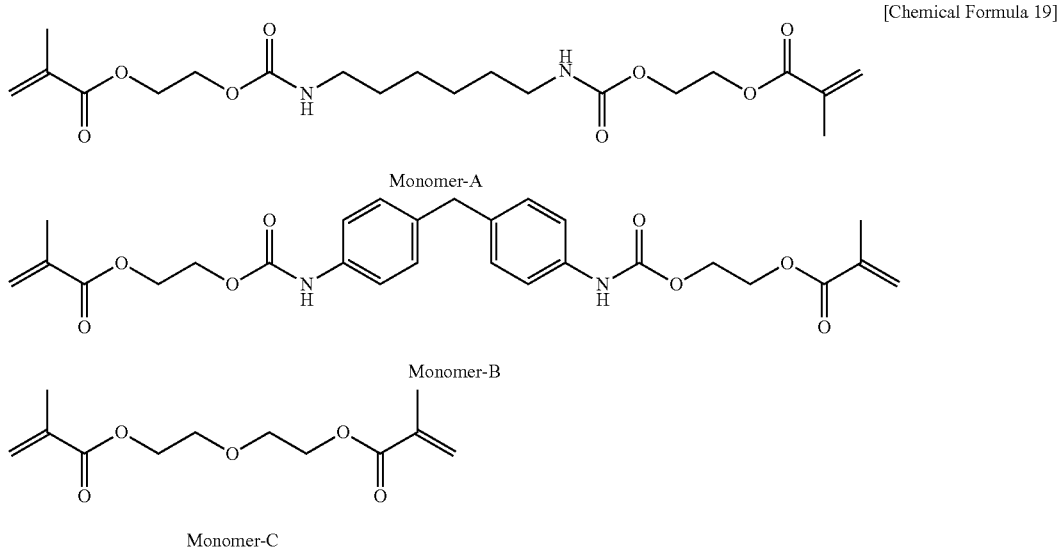

[Chemical Formula 19]

Monomer-A

Monomer-B

Monomer-C

Comparative Examples 21-1

(Preparation of Medical and/or Dental Composite Resins)

Using the silane coupling agent synthesized in Comparative Synthesis Example 11, surface modification with OX-50 (manufactured by NIPPON AEROSIL CO., LTD.) and Fuselex (manufactured by TATSUMORI LTD.) and preparation of medical and/or dental composite resins were performed. Specific surface modification method will be mentioned below. A silane coupling agent in the amount mentioned in Tables 21-1 was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (Monomer-A, —C) and a photopolymerization initiator mentioned in Table 21-1 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

Comparative Examples 22-1

(Preparation of Medical and/or Dental Composite Resins)

Using the silane coupling agent synthesized in Comparative Synthesis Example 11, surface modification with OX-50 (manufactured by NIPPON AEROSIL CO., LTD.) and Fuselex (manufactured by TATSUMORI LTD.) and preparation of medical and/or dental composite resins were performed. Specific surface modification method will be mentioned below. A silane coupling agent in the amount mentioned in Tables 21-2 was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (Monomer-B, -C) and a photopolymerization initiator mentioned in Table 21-2 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

Bending Strength Test

Using medical and/or dental composite resins prepared in Examples 11-1 to 11-5, 12-1 to 12-5, 21-1 to 21-7, 22-1 to 22-7, Comparative Examples 11-1 to 11-3, 12-1 to 12-3, 21-1 and 22-1, cured bodies were fabricated in accordance with ISO4049. Using an Instron universal testing machine (Instron 5567, manufactured by Instron Corporation), the bending strength was determined. Photopolymerization was performed by photoirradiation for 30 seconds using Griplight II manufactured by SHOFU INC.

Color Tone Stability Test of Silane Coupling Agent

Each of 9.0 ml of silane coupling agents synthesized in Synthesis Examples 11 to 15 and 21 to 25, and Comparative Synthesis Example 11 and two types of polymerizable silane coupling agents [KBM-503: 3-(trimethoxysilyl)propyl methacrylate (also referred to as "C-SC11"), KBE-503: 3-(triethoxysilyl)propyl methacrylate (also referred to as "C-SC12")] available from Shin-Etsu Chemical Co., Ltd. was transferred to a 10 mL-volume colorless transparent glass vial and then the Hazen color index was measured. After storing the same sample under a shading condition in a thermostat at 50° C. for a month, the Hazen color index was measured.

Color Tone Stability Test of Medical and/or Dental Composite Resin Cured Bodies Fabricated Using medical and/or dental composite resins thus prepared, cured bodies (circular disk of 15 mm in diameter and 1.0 mm in thickness) were fabricated in accordance with ISO4049, and then the color tone stability of each cured body was determined by a light resistance tester (Atlas SUNTEST CPS+, manufactured by TOYO SEIKI SEISAKU-SHO, LTD.). Photopolymerization was performed by photoirradiation for 30 seconds using Griplight II manufactured by SHOFU INC.

Evaluation Results

The bending strength test results of medical and/or dental composite resins prepared based on Examples 11-1 to 11-5 and 12-1 to 12-5 are shown in Table 12-1. As is apparent from these results, medical and/or dental composite resins including fine particles prepared using silane coupling agents synthesized (Synthesis Examples 11 to 15) by the present invention have obviously high bending strength properties as compared with medical and/or dental composite resins using conventional silane coupling agents (Comparative Synthesis Examples 11-1 to 11-3 and 12-1 to 12-3). It is particularly apparent that breaking energy properties are significantly improved. In other words, by surface-treating an inorganic filler with the silane coupling agent of the embodiments of the present invention, a medical and/or dental composite resin cured body exhibits toughness, thus imparting high mechanical strength to a medical and/or dental composite resins. It is assumed that this is the result of the presence of a long-chain alkylene group and/or multiple urethane groups. As is apparent from the above evaluation results(results of Bending Strength Test), the silane coupling agent having a long-chain alkylene group and/or multiple urethane groups in the present invention made it possible to provide a medical and/or dental curable composition having high mechanical strength that could not been achieved by the prior art, and applications thereof in the general industrial field such as for bonding of electronic component material substrates including smartphones and automotive materials.

The measurement results of the Hazen color index determined by a color tone stability test are shown in Table 12-2. As is apparent from these measurement results, there was no large difference in Hazen color index between the polymerizable silane coupling agents including no platinum complex synthesized in Synthesis Examples 11 to 15 (SC11 to SC15) and two types of polymerizable silane coupling agents [3-(trimethoxysilyl)propyl methacrylate (C-SC11), 3-(triethoxysilyl)propyl methacrylate(C-SC12)] available from Shin-Etsu Chemical Co., Ltd., immediately after synthesis and purchasing, and after storing under a shading condition at 50° C. for a month. Meanwhile, there was a large difference in Hazen color index between the polymerizable silane coupling agent including a platinum complex synthesized in Comparative Synthesis Example 11 (C-SC13), immediately after synthesis, and after storing under a shading condition at 50° C. for a month. It is considered that this large change in color tone is attributed to the remaining platinum complex.

Subsequently, the measurement results relating to the color tone stability of the cured body are shown in Table 12-3. As is apparent from these measurement results, there was no large change in color tone of the medical and/or dental composite resin cured bodies including an inorganic filler surface-modified with the polymerizable silane coupling agents including no platinum complex synthesized in Synthesis Examples 11 to 15 and two types of polymerizable silane coupling agents [3-(trimethoxysilyl)propyl methacrylate, 3-(triethoxysilyl)propyl methacrylate] available from Shin-Etsu Chemical Co., Ltd. Meanwhile, there arose a large difference in color tone of the medical and/or dental composite resin cured body including an inorganic filler surface-modified with the polymerizable silane coupling agents including a platinum complex synthesized in Comparative Synthesis Example 11, leading to remarkable yellowing.

As is apparent from these test results, it is revolutionary in that no discoloration due to noble metal is not observed in the medical and/or dental curable composition, which is aesthetically important. Since no noble metal as a hydrosilylation catalyst is used during synthesis, it became possible to decrease manufacturing costs. Furthermore, since the solubility of reagents in organic solvents during synthesis was remarkably improved by using compounds with isocyanate groups at both ends as reaction substrates, the urethane reaction could be performed at a higher temperature than the case using 1-10-decanediol. This led to a reduction in the reaction time, which in turn led to a reduction in the production cost.

TABLE 11-1

Filling rate 70 wt %
Unit: g

| | Example 11-1 | Example 11-2 | Example 11-3 | Example 11-4 | Example 11-5 | Comparative Example 11-1 | Comparative Example 11-2 | Comparative Example 11-3 |
|---|---|---|---|---|---|---|---|---|
| SC11 | 8.48 | — | — | — | — | — | — | — |
| SC12 | — | 9.26 | — | — | — | — | — | — |
| SC13 | — | — | 9.22 | — | — | — | — | — |
| SC14 | — | — | — | 8.23 | — | — | — | — |
| SC15 | — | — | — | — | 7.73 | — | — | — |
| C-SC11 | — | — | — | — | — | 4.40 | — | — |
| C-SC12 | — | — | — | — | — | — | 5.14 | — |
| C-SC13 | — | — | — | — | — | — | — | 8.67 |
| OX-50 | 15.0 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 | 40.0 |

TABLE 11-1-continued

Filling rate 70 wt %
Unit: g

|  | Example 11-1 | Example 11-2 | Example 11-3 | Example 11-4 | Example 11-5 | Comparative Example 11-1 | Comparative Example 11-2 | Comparative Example 11-3 |
|---|---|---|---|---|---|---|---|---|
| UDMA | 16.5 | 16.5 | 16.5 | 16.5 | 16.5 | 16.5 | 16.5 | 16.5 |
| 2G | 7.1 | 7.1 | 7.1 | 7.1 | 7.1 | 7.1 | 7.1 | 7.1 |
| Initiator | 0.24 | 0.24 | 0.24 | 0.24 | 0.24 | 0.24 | 0.24 | 0.24 |

SC11: Radical polymerizable silane coupling agent synthesized in synthesis example 11
SC12: Radical polymerizable silane coupling agent synthesized in synthesis example 12
SC13: Radical polymerizable silane coupling agent synthesized in synthesis example 13
SC14: Radical polymerizable silane coupling agent synthesized in synthesis example 14
SC15: Radical polymerizable silane coupling agent synthesized in synthesis example 15
C-SC11: 3-(trimethoxysilyl)propyl methacrylate
C-SC12: 3-(triethoxysilyl)propyl methacrylate
C-SC13: Radical polymerizable silane coupling agent synthesized in comparative synthesis example 11
UDMA: Di(methacryloxyethyl)trimethyl hexamethylene diurethane
2G: Diethylene glycol dimethacrylate
Initiator: Diphenyl(2,4,6-trimethylbenzoyl)phosphine oxide

TABLE 11-2

Filling rate 85 wt %
Unit: g

|  | Example 12-1 | Example 12-2 | Example 12-3 | Example 12-4 | Example 12-5 | Comparative Example 12-1 | Comparative Example 12-2 | Comparative Example 12-3 |
|---|---|---|---|---|---|---|---|---|
| SC11 | 8.48 | — | — | — | — | — | — | — |
| SC12 | — | 9.26 | — | — | — | — | — | — |
| SC13 | — | — | 9.22 | — | — | — | — | — |
| SC14 | — | — | — | 8.23 | — | — | — | — |
| SC15 | — | — | — | — | 7.73 | — | — | — |
| C-SC11 | — | — | — | — | — | 4.40 | — | — |
| C-SC12 | — | — | — | — | — | — | 5.14 | — |
| C-SC13 | — | — | — | — | — | — | — | 8.67 |
| OX-50 | 15.0 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 | 40.0 |
| UDMA | 6.8 | 6.8 | 6.8 | 6.8 | 6.8 | 6.8 | 6.8 | 6.8 |
| 2G | 2.9 | 2.9 | 2.9 | 2.9 | 2.9 | 2.9 | 2.9 | 2.9 |
| Initiator | 0.1 | 0.1 | 0.1 | 0.1 | 0.1 | 0.1 | 0.1 | 0.1 |

SC11: Radical polymerizable silane coupling agent synthesized in synthesis example 11
SC12: Radical polymerizable silane coupling agent synthesized in synthesis example 12
SC13: Radical polymerizable silane coupling agent synthesized in synthesis example 13
SC14: Radical polymerizable silane coupling agent synthesized in synthesis example 14
SC15: Radical polymerizable silane coupling agent synthesized in synthesis example 15
C-SC11: 3-(trimethoxysilyl)propyl methacrylate
C-SC12: 3-(triethoxysilyl)propyl methacrylate
C-SC13: Radical polymerizable silane coupling agent synthesized in comparative synthesis example 11.
UDMA: Di(methacryloxyethyl)trimethyl hexamethylene diurethane
2G: Diethylene glycol dimethacrylate
Initiator: Diphenyl(2,4,6-trimethylbenzoyl)phosphine oxide

TABLE 12-1

Bending test results (bending stress: MPa, breaking energy: Kgf-mm, strain: %)

|  | Example 11-1 | Example 11-2 | Example 11-3 | Example 11-4 | Example 11-5 | Comparative Example 11-1 | Comparative Example 11-2 | Comparative Example 11-3 |
|---|---|---|---|---|---|---|---|---|
| Bending stress | 140 | 14.4 | 143 | 139 | 138 | 105 | 106 | 135 |
| Breaking energy | 2.78 | 2.90 | 2.91 | 2.68 | 2.55 | 1.23 | 1.25 | 2.30 |

TABLE 12-1-continued

Bending test results (bending stress: MPa, breaking energy: Kgf-mm, strain: %)

|  | Example 12-1 | Example 12-2 | Example 12-3 | Example 12-4 | Example 12-5 | Comparative Example 12-1 | Comparative Example 12-2 | Comparative Example 12-3 |
|---|---|---|---|---|---|---|---|---|
| Bending stress | 153 | 158 | 156 | 154 | 152 | 115 | 113 | 148 |
| Breaking energy | 3.01 | 3.21 | 3.21 | 2.99 | 2.83 | 1.35 | 1.31 | 2.55 |

TABLE 12-2

Hazen Color Index

|  | SC11 | SC12 | SC13 | SC14 | SC15 | C-SC11 | C-SC12 | C-SC13 |
|---|---|---|---|---|---|---|---|---|
| Immediately after synthesis | 16 | 16 | 16 | 16 | 16 | 12 | 12 | 20 |
| After 1 month at 50° C. | 21 | 20 | 21 | 21 | 21 | 18 | 19 | 300 |

TABLE 12-3

Color Tone Stability for Cured Body (L/a*/b*)

|  | Example 11-1 | Example 11-2 | Example 11-3 | Example 11-4 | Example 11-5 |
|---|---|---|---|---|---|
| Control | 80.0/−2.0/5.0 | 80.0/−2.0/5.0 | 80.0/−2.0/5.0 | 80.0/−2.0/5.0 | 80.0/−2.0/5.0 |
| In water | 79.9/−2.1/5.1 | 79.9/−2.0/5.1 | 79.9/−2.1/5.0 | 79.9/−2.1/5.1 | 79.9/−2.1/5.1 |
| After photoirradiation | 79.0/−3.0/5.2 | 79.0/−3.0/5.2 | 79.2/−3.0/5.2 | 79.0/−3.0/5.2 | 79.1/−3.0/5.1 |

|  | Comparative Example 11-1 | Comparative Example 11-2 | Comparative Example 11-3 |
|---|---|---|---|
| Control | 80.0/−2.0/5.0 | 80.0/−2.0/5.0 | 80.0/−2.0/5.0 |
| In water | 79.9/−2.1/5.0 | 80.0/−2.0/5.1 | 75.9/−2.9/5.1 |
| After photoirradiation | 79.0/−2.9/5.3 | 79.2/−3.0/5.2 | 72.1/−3.9/5.9 |

Evaluation Results

The bending strength test results of medical and/or dental composite resins prepared based on Examples are shown in Table 22-1. From these results, significant differences were clearly observed especially in the composite resins (Examples 22-1 to 22-5) using a monomer having a benzene ring and/or a cyclohexane ring (Monomer-B) in its molecular skeleton. That is, medical and/or dental composite resins containing fine particles prepared using a silane coupling agent having a benzene ring and/or a cyclohexane ring in its base skeleton synthesized in the present invention (Synthesis Examples 21 to 25) have obviously higher bending strength properties as compared with medical and/or dental composite resins using conventional silane coupling agents (Comparative Synthesis Examples 21-1 to 22-1). It is particularly apparent that breaking energy properties are significantly improved. In other words, by surface-treating an inorganic filler with the silane coupling agent of the embodiments of the present invention, a medical and/or dental composite resin cured body exhibits toughness, thus imparting high mechanical strength to a medical and/or dental composite resins. It is assumed that this is the result of the introduction of a benzene ring and/or a cyclohexane ring to a base skeleton in addition to the presence of multiple urethane groups. As is apparent from the above evaluation results (results of Bending Strength Test), the silane coupling agent having a benzene ring and/or a cyclohexane ring and also having two urethane groups in the present invention made it possible to provide a medical and/or dental curable composition having high mechanical strength that could not been achieved by the prior art, and applications thereof in the general industrial field such as for bonding of electronic component material substrates including smartphones and automotive materials.

The measurement results of the Hazen color index determined by a color tone stability test are shown in Table 22-2. As is apparent from these measurement results, there was no large difference in Hazen color index between the polymerizable silane coupling agents including no platinum complex synthesized in Synthesis Examples 21 to 25 immediately after synthesis, and after storing under a shading condition at 50° C. for a month. Meanwhile, there was a large difference in Hazen color index between the polymerizable silane coupling agent including a platinum complex synthesized in Comparative Synthesis Example 11 immediately after synthesis, and after storing under a shading condition at 50° C. for a month. It is considered that this large change in color tone is attributed to the remaining platinum complex.

Subsequently, the measurement results relating to the color tone stability of the cured body are shown in Table 22-3. As is apparent from these measurement results, there was no large change in color tone of the medical and/or dental composite resin cured bodies including an inorganic filler surface-modified with the polymerizable silane coupling agents including no platinum complex synthesized in Synthesis Examples 21 to 25. Meanwhile, there arose a large difference in color tone of the medical and/or dental composite resin cured body including an inorganic filler surface-modified with the polymerizable silane coupling agents including a platinum complex synthesized in Comparative Synthesis Example 11, leading to remarkable yellowing.

As is apparent from these test results, it is revolutionary in that no discoloration due to noble metal is not observed in the medical and/or dental curable composition, which is aesthetically important. Since no noble metal as a hydrosilylation catalyst is used during synthesis, it became possible to decrease manufacturing costs. Furthermore, since the solubility of reagents in organic solvents during synthesis was remarkably improved by using compounds with isocyanate groups at both ends as reaction substrates, the urethane reaction could be performed at a higher temperature than the case using 1-10-decanediol. This led to a reduction in the reaction time, which in turn led to a reduction in the production cost.

TABLE 21-1

Filling rate 85 wt %
Unit: g

|  | Example 21-1 | Example 21-2 | Example 21-3 | Example 21-4 | Example 21-5 | Example 21-6 | Example 21-7 | Comparative Example 21-1 |
|---|---|---|---|---|---|---|---|---|
| SC21 | 10.67 | — | — | — | — | — | — | — |
| SC22 | — | 11.17 | — | — | — | — | — | — |
| SC23 | — | — | 9.33 | — | — | — | — | — |
| SC24 | — | — | — | 8.69 | — | — | — | — |
| SC25 | — | — | — | — | 9.33 | — | — | — |
| SC11 | — | — | — | — | — | 8.48 | — | — |
| SC12 | — | — | — | — | — | — | 9.26 | — |
| C-SC13 | — | — | — | — | — | — | — | 7.93 |
| OX-50 | 15.0 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 | 40.0 |
| Monomer-A | 6.8 | 6.8 | 6.8 | 6.8 | 6.8 | 6.8 | 6.8 | 6.8 |
| Monomer-C | 2.9 | 2.9 | 2.9 | 2.9 | 2.9 | 2.9 | 2.9 | 2.9 |
| Initiator | 0.1 | 0.1 | 0.1 | 0.1 | 0.1 | 0.1 | 0.1 | 0.1 |

SC21: Radical polymerizable silane coupling agent synthesized in synthesis example 21
SC22: Radical polymerizable silane coupling agent synthesized in synthesis example 22
SC23: Radical polymerizable silane coupling agent synthesized in synthesis example 23
SC24: Radical polymerizable silane coupling agent synthesized in synthesis example 24
SC25: Radical polymerizable silane coupling agent synthesized in synthesis example 25
SC11: Radical polymerizable silane coupling agent synthesized in synthesis example 11
SC12: Radical polymerizable silane coupling agent synthesized in synthesis example 12
C-SC13: Radical polymerizable silane coupling agent synthesized in comparative synthesis example 11
Monomer-A: 4,13-Dioxo-3,14-dioxa-5,12-diazahexadecane-1,16-diyl bis(2-methacrylate)
Monomer-C: Oxybis(ethane-2,l-diyl)bis(2-methacrylate)
Initiator: Diphenyl(2,4,6-trimethylbenzoyl)phosphine oxide

TABLE 21-2

Filling rate 85 wt %
Unit: g

|  | Example 22-1 | Example 22-2 | Example 22-3 | Example 22-4 | Example 22-5 | Example 22-6 | Example 22-7 | Comparative Example 22-1 |
|---|---|---|---|---|---|---|---|---|
| SC21 | 10.67 | — | — | — | — | — | — | — |
| SC22 | — | 11.17 | — | — | — | — | — | — |
| SC23 | — | — | 9.33 | — | — | — | — | — |
| SC24 | — | — | — | 8.69 | — | — | — | — |
| SC25 | — | — | — | — | 9.33 | — | — | — |
| SC11 | — | — | — | — | — | 8.48 | — | — |
| SC12 | — | — | — | — | — | — | 9.26 | — |
| C-SC13 | — | — | — | — | — | — | — | 7.93 |
| OX-50 | 15.0 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 | 40.0 |

TABLE 21-2-continued

Filling rate 85 wt %
Unit: g

|  | Example 22-1 | Example 22-2 | Example 22-3 | Example 22-4 | Example 22-5 | Example 22-6 | Example 22-7 | Comparative Example 22-1 |
|---|---|---|---|---|---|---|---|---|
| Monomer-B | 6.8 | 6.8 | 6.8 | 6.8 | 6.8 | 6.8 | 6.8 | 6.8 |
| Monomer-C | 2.9 | 2.9 | 2.9 | 2.9 | 2.9 | 2.9 | 2.9 | 2.9 |
| Initiator | 0.1 | 0.1 | 0.1 | 0.1 | 0.1 | 0.1 | 0.1 | 0.1 |

SC21: Radical polymerizable silane coupling agent synthesized in synthesis example 21
SC22: Radical polymerizable silane coupling agent synthesized in synthesis example 22
SC23: Radical polymerizable silane coupling agent synthesized in synthesis example 23
SC24: Radical polymerizable silane coupling agent synthesized in synthesis example 24
SC25: Radical polymerizable silane coupling agent synthesized in synthesis example 25
SC11: Radical polymerizable silane coupling agent synthesized in synthesis example 11
SC12: Radical polymerizable silane coupling agent synthesized in synthesis example 12
C-SC13: Radical polymerizable silane coupling agent synthesized in comparative synthesis example 11
Monomer-B: ((((Methylenebis(4,1-phenylene))bis(azanediyl))bis(carbonyl))bis(oxy))bis(ethane-2,1-diyl)bis(2-methacrylate)
Monomer-C: Oxybis(ethane-2,1-diyl)bis(2-methacrylate)
Initiator: Diphenyl(2,4,6-trimethylbenzoyl)phosphine oxide

TABLE 22-1

Bending test results (bending stress: MPa, breaking energy: Kgf-mm, strain: %)

|  | Example 21-1 | Example 21-2 | Example 21-3 | Example 21-4 | Example 21-5 | Example 21-6 | Example 21-7 | Comparative Example 21-1 |
|---|---|---|---|---|---|---|---|---|
| Bending stress | 139 | 137 | 138 | 135 | 138 | 134 | 135 | 135 |
| Breaking energy | 2.73 | 2.72 | 2.79 | 2.71 | 2.73 | 2.77 | 2.75 | 2.71 |

|  | Example 22-1 | Example 22-2 | Example 22-3 | Example 22-4 | Example 22-5 | Example 22-6 | Example 22-7 | Comparative Example 22-1 |
|---|---|---|---|---|---|---|---|---|
| Bending stress | 152 | 159 | 155 | 147 | 156 | 139 | 139 | 140 |
| Breaking energy | 3.01 | 3.22 | 3.21 | 3.11 | 3.25 | 2.81 | 2.79 | 2.72 |

TABLE 22-2

Hazen Color Index

|  | SC21 | SC22 | SC23 | SC24 | SC25 | SC11 | SC12 | C-SC13 |
|---|---|---|---|---|---|---|---|---|
| Immediately after synthesis | 16 | 16 | 17 | 16 | 16 | 16 | 16 | 20 |
| After 1 month at 50° C. | 20 | 20 | 21 | 21 | 20 | 21 | 20 | 300 |

TABLE 22-3

Color Tone Stability for Cured Body(L/a*/b*)

|  | Example 21-1 | Example 21-2 | Example 21-3 | Example 21-4 | Example 21-5 |
|---|---|---|---|---|---|
| Control | 80.0/−2.0/5.0 | 80.0/−2.0/5.0 | 80.0/−2.0/5.0 | 80.0/−2.0/5.0 | 80.0/−2.0/5.0 |
| In water | 79.9/−2.1/5.1 | 79.9/−2.0/5.0 | 79.9/−2.1/5.0 | 79.9/−2.1/5.1 | 79.9/−2.1/5.1 |
| After photoirradiation | 79.0/−3.0/5.1 | 79.0/−3.0/5.1 | 79.3/−3.0/5.2 | 79.0/−3.0/5.1 | 79.6/−3.0/5.1 |

TABLE 22-3-continued

| | Color Tone Stability for Cured Body(L/a*/b*) | | |
|---|---|---|---|
| | Example 21-6 | Example 21-7 | Comparative Example 21-1 |
| Control | 80.0/−2.0/5.0 | 80.0/−2.0/5.0 | 80.0/−2.0/5.0 |
| In water | 79.9/−2.1/5.1 | 80.0/−2.0/5.0 | 76.0/−2.9/5.1 |
| After photoirradiation | 79.1/−2.9/5.3 | 79.2/−3.0/5.2 | 71.1/−3.9/5.7 |

INDUSTRIAL APPLICABILITY

Silane coupling agents currently in use are not limited to the medical and dental fields, but also to general industrial fields, and are generally low molecular weight type such as 3-(trimethoxysilyl)propyl methacrylate. In addition, silane coupling agents with a long alkylene chain are used to further improve various properties. However, although these silane coupling agents with long alkylene chains are more effective than low-molecular-weight silane coupling agents (eg. alkylene chain number: 3) in improving various properties, they are significantly inferior in terms of discoloration, etc., because they require a hydrosilylation reaction using a precious metal catalyst during synthesis. The silane coupling agents in the present inventions overcome all of these problems.

Furthermore, by using diisocyanate (preferably diisocyanate with a benzene ring and/or cyclohexane ring) for which toluene or the like is a good solvent, as a reaction substrate, the number of organic selectable solvents increases in comparison with organic-solvent-poor-solubility compounds such as 1-10-decanediol. In other words, this present invention has a great industrial applicability from the perspective of reducing manufacturing costs by allowing the selection of higher temperatures for the urethane reaction, and from the perspective of a high affinity for radical polymerizable group monomers having benzene and/or cyclohexane rings.

The invention claimed is:

1. A silane coupling agent having a polymerizable group, which is represented by the following formula

[Chemical Formula 1]

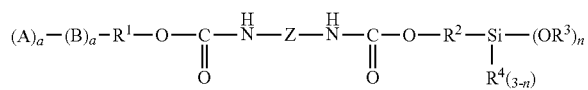

A represents a $H_2C=CH-$, $H_2C=C(CH_3)-$, or $H_2C=CH-C_6H_4-$ group where $C_6H_4$ represents a phenylene group, B represents a $-C(O)-O-$, $-C(O)-S-$, $-C(O)-NH-$, $-NH-C(O)-NH-$, $-NH-C(O)-S-$, or $-NH-C(O)-O-$ group, $R^1$ represents a C2 to C100 linear or branched alkylene group and may comprise one or more of a $-O-CH_2-CH_2-$, $-O-CH(CH_3)-CH_2-$ and/or $-CH(CH_3)-CH_2-O-$ groups, Z comprises at least one or more a benzene ring or a cyclohexane ring and/or a C2 to C100 linear or branched alkylene group, $R^2$ represents a C2 to C100 linear or branched alkylene group, $R^3$ represents a C1 to C6 linear or branched alkyl group, $R^4$ represents a C1 to C16 linear or branched alkyl group, a phenyl group, or a halogen atom, and when n is 0, at least one or more of halogen atoms are bonded to Si, a is 1 to 6 and n is 0 to 3.

2. An inorganic filler which is surface-treated with the silane coupling agent according to claim 1.

3. A medical and/or dental curable composition comprising the inorganic filler according to claim 2, a radical polymerizable monomer and at least one of a polymerization initiator and/or a polymerization accelerator.

4. A medical and/or dental curable composition according to claim 3, characterized in that the radical polymerizable monomer has at least one of a benzene ring and/or a cyclohexane ring in its molecular skeleton.

* * * * *